United States Patent
Roy et al.

(10) Patent No.: US 8,946,261 B2
(45) Date of Patent: Feb. 3, 2015

(54) SUBSTITUTED 1, 2, 3, 4-TETRAHYDROQUINOLIN-7-YL CARBAMATES AS ACETYLCHOLINESTERASE INHIBITORS FOR TREATMENT OF ALZHEIMER'S DISEASE

(75) Inventors: Kuldeep Kumar Roy, Lucknow (IN); Santoshkumar Tota, Lucknow (IN); Chandishwar Nath, Lucknow (IN); Rakesh Shukla, Lucknow (IN); Anil Kumar Saxena, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/984,998

(22) PCT Filed: Jan. 24, 2012

(86) PCT No.: PCT/IN2012/000053
§ 371 (c)(1),
(2), (4) Date: Aug. 12, 2013

(87) PCT Pub. No.: WO2012/111021
PCT Pub. Date: Aug. 23, 2012

(65) Prior Publication Data
US 2013/0324573 A1 Dec. 5, 2013

(30) Foreign Application Priority Data
Feb. 14, 2011 (IN) .............................. 363/DEL/2011

(51) Int. Cl.
C07D 215/20 (2006.01)
A61K 31/04 (2006.01)

(52) U.S. Cl.
CPC ................................... C07D 215/20 (2013.01)
USPC .......................................... 514/313; 546/165

(58) Field of Classification Search
USPC .......................................... 546/165; 514/313
See application file for complete search history.

(56) References Cited

U.S. PATENT DOCUMENTS

2006/0142335 A1 6/2006 Shakya et al.

OTHER PUBLICATIONS

Xiao, Org Lett, vol. 11(13), pp. 2876-2879, 2009.*
S. S. Chaudhaery et al. "Novel Carbamates as Orally Active Acetylcholinesterase Inhibitors Found to Improve Scopolamine-Induced Cognition Impairment; Pharmacophore-Based Virtual Screening, Synthesis and Pharmacology," Journal of Medicinal Chemistry, 53(17), 6490-6505 (2010).
Chemical Abstract Registry No. 773794-77-7, entered Nov. 1, 2004 (XP-00671626).

* cited by examiner

*Primary Examiner* — D M Seaman
(74) *Attorney, Agent, or Firm* — Edwards Wildman Palmer LLP; Barry Kramer; Nicholas J. DiCeglie, Jr.

(57) ABSTRACT

The present invention relates to novel substituted 1,2,3,4-tetrahydroquinolin-7-yl carbamates, their preparation, and use as therapeutic agents, particularly in the prevention or treatment of neurodegenerative or Alzheimer's disease, or senile dementia, or memory disturbances, and more particularly to the prevention, treatment and amelioration of Alzheimer's disease with the novel substituted 1,2,3,4-tetrahydroquinolin-7-yl carbamates, which act as inhibitors of central cholinesterase enzymes, particularly acetylcholinesterase (AChE) following the indirect cholinomimetic pathway. The present invention particularly relates to compounds of formula A: Formula A wherein $R_1$=alkyl, aryl, substituted aryl; $R_2$=H, methyl; $R_3$=H, alkyl, alkenyl, alkynyl, aralkyl, substituted aralkyl, aryl, heteroaryl.

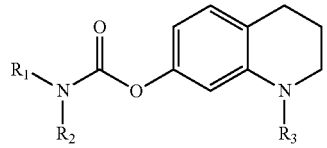

Formula A

21 Claims, 3 Drawing Sheets

SUBSTITUTED 1, 2, 3, 4-TETRAHYDROQUINOLIN-7-YL CARBAMATES AS ACETYLCHOLINESTERASE INHIBITORS FOR TREATMENT OF ALZHEIMER'S DISEASE

CROSS REFERENCE TO RELATED APPLICATIONS

This application is a 371 U.S. National Phase Application of PCT/IN2012/00053, filed Jan. 24, 2012, which claims priority to Indian Patent Application No. 363/DEL/2011, filed Feb. 14, 2011, the disclosures of each of which are expressly incorporated herein by reference in their entireties.

FIELD OF INVENTION

The present invention relates to novel substituted 1,2,3,4-tetrahydroquinolin-7-yl carbamates, their preparation, to pharmaceutical compositions comprising them and to their use as therapeutic agents, particularly in the prevention or treatment of neurodegenerative or Alzheimer's disease, or senile dementia, or memory disturbances, and more particularly to the prevention, treatment and amelioration of Alzheimer's disease (AD) with the novel substituted 1,2,3,4-tetrahydroquinolin-7-yl carbamates, which act as inhibitors of central cholinesterase enzymes, particularly acetylcholinesterase (AChE) following the indirect cholinomimetic pathway. The present invention particularly relates to compounds of formula A:

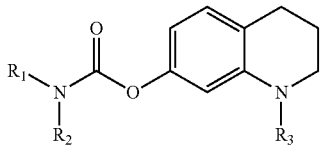

Formula A

Wherein $R_1$ and $R_2$, are independently selected from group consisting of hydrogen, saturated or unsaturated alkyl ($C_1$-$C_7$), aryl such as substituted or unsubstituted phenyl.
$R_3$ is selected from the group consisting of hydrogen, saturated or unsaturated alkyl (C1-C3), aralkyl such as benzyl, alkynyl such as propargyl.

BACKGROUND OF INVENTION

Alzheimer's disease (AD) is a devastating chronic and progressive neurological disorder that affects more than 37 million people worldwide (Mount, C. and Downton, C. *Nature Med.* 2006, 12, 780-784). It is clinically characterized by progressive cognitive impairments or decline defined by a loss of memory and learning ability, together with a reduced ability to perform daily routine activities and a diverse array of neuropsychiatric symptoms such as apathy, verbal and physical agitation, irritability, anxiety, depression, delusions and hallucinations. Two forms of AD exist: a familial one (multiple family members are affected) and a sporadic one, in which one or a few members of a family develop the disease. The number of AD affected persons is expected to triple or quadruple by 2050 and expected to become the developed world's largest socioeconomic healthcare burden over the coming decades (Mount, C. and Downton, C. *Nature Med.* 2006, 12, 780-784). Characteristic neuropathologic findings include selective neuronal and synaptic losses, extracellular neuritic plaques containing the β-amyloid peptide and neurofibrillary tangles (NFTs) composed of hyperphosphorylated forms of the tau (τ) protein (Klafki, H. W. et al. *Brain* 2006, 129, 2840-2855). Current medications that have passed FDA approval for the treatment of Alzheimer's disease include acetylcholinesterase (AChE) inhibitors, namely, Tacrine, Rivastigmine, Donepezil, and Galantamine for mild to moderate cases, and N-methyl-D-aspartate (NMDA)-receptor antagonist memantine for the treatment of moderate to severe Alzheimer's disease.

Apart from above mentioned drugs, extensive efforts toward the novel cholinesterase inhibitors have led to few more potent compounds such as Xanthostigmine, Physostigmine, Phenserine, Huperzine-A, Bis-tacrine, Bis-huperzin-B, Quilostigmine, Eptastigmine, Ro-46-5934, P10358, CHF2819 etc. Apart from this, some pyridinium or quinolinium carbamate derivatives have been disclosed as AChE inhibitors in US2009/0062279, in WO97/08146. Nevertheless, these compounds present the drawback of being unstable in vivo and very rapidly deactivated.

In the recent past, we have disclosed substituted carbamic acid quinolin-6-yl esters as orally effective AChE inhibitors in WO2006/070394; in US2006/0142335; and in Chaudhary, S. S. et al. *J. Med. Chem.* 2010, 53, 6490-6505.

Current drugs for Alzheimer's disease, namely, tacrine, donepezil, rivastigmine, galanthamine and memantine are not able to alter or prevent disease progression and suffer from major drawback of loss of therapeutic potential with time. They are, instead, palliative in alleviating disease symptoms (Melnikova, I. *Nat. Rev. Drug Discovery* 2007, 6, 341-342). Thus, increasing daily doses in such circumstances increases the side effects until the pause of the treatment. The major side effects are specifically caused by the peripheral activity of these drugs on cholinesterase enzyme.

As the average age is increasing all over the world, and so the AD (66% in the developing countries), there is an urgent need for novel therapeutics which could act as anti-Alzheimer agents with low or no side effects associated with the known commercial drugs for the treatment of Alzheimer's disease. Specifically, there is a need for new cholinesterase inhibitors with wider therapeutic window, to be useful as potential anti-Alzheimer agents without interacting with peripheral cholinesterase enzyme.

OBJECTS OF INVENTION

The principal object of the present invention is to provide novel cholinesterase inhibitors incorporating 1,2,3,4-tetrahydroquinoline flanked on one side at position 7 by substituted aryl/alkyl carbamate/carbamic acid ester and on the other side at position 1 by hydrogen or alkyl, or alkynyl or aralkyl, which are of outstanding therapeutic efficacy to treat neurodegenerative diseases, particularly Alzheimer's disease or senile dementia.

It is another object of the invention is to provide a method for the treatment of Alzheimer's disease.

It is further object of the present invention to provide candidate molecules useful for the treatment or prevention of senile dementia of Alzheimer's type, cerebral dementia, vascular dementia, alcoholic dementia, dementia associated with neurological disorders like epilepsy, neoplasm, post-trauma etc and dementia related with behavioral disorders like depression, psychosis etc.

It is another object of invention to provide compounds useful for the treatment or management or prevention of atony of the smooth muscle of the intestinal tract (paralytic ileus) and atony of the urinary bladder.

It is another object of invention to provide compounds useful for the treatment or prevention of glaucoma or myasthenia gravis.

SUMMARY OF INVENTION

Accordingly, present invention provides a compound of general formula A:

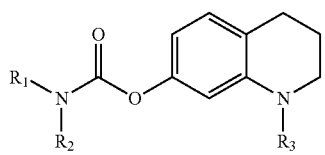

Formula A wherein:
$R_1$ and $R_2$, independently selected from the group consisting of hydrogen, saturated) unsaturated alkyl ($C_1$-$C_7$), and aryl;
$R_3$ is selected from the group consisting of hydrogen, saturated/unsaturated alkyl (C1-C3), aralkyl such as benzyl, alkynyl such as propargyl.

In an embodiment of the present invention R1 is alkyl, selected from the group consisting of methyl, isopropyl, hexyl and heptyl.

In another embodiment of the present invention $R_1$ is aryl selected from group consisting of 2-chlorophenyl, 3-chlorophenyl, 4-chlorophenyl, 2-bromophenyl, 3-bromophenyl, 4-bromophenyl 2-fluorophenyl, 4-fluorophenyl, 2-isopropylphenyl, 2-methoxyphenyl, 4-methoxyphenyl, 2-methylphenyl, 3-methylphenyl, 4-methylphenyl, 6-methylphenyl, and 2-isopropyl-6-methylphenyl.

In another embodiment of the present invention wherein $R_1$ is alkyl, $R_2$ is selected from the group consisting of hydrogen, methyl and isopropyl.

In still another embodiment of the present invention when R1 is substituted or unsubstituted aryl e.g. 2-chlorophenyl, 3-chlorophenyl, 4-chlorophenyl, 2-bromophenyl, 3-bromophenyl, 4-bromophenyl, 2-fluorophenyl, 4-fluorophenyl, 2-isopropylphenyl, 2-methoxyphenyl, 4-methoxyphenyl, 2-methylphenyl, 3-methylphenyl, 4-methylphenyl, and 2-isopropyl-6-methylphenyl, the $R_2$ group is hydrogen.

In yet another embodiment of the present invention $R_3$ is selected from the group consisting of hydrogen methyl, prop-2-ynyl (or propargyl), and benzyl.

The representative compounds of general formula A comprising:
1-benzyl-1,2,3,4-tetrahydroquinolin-7-yl 2-methylphenylcarbamate 8a;
1-benzyl-1,2,3,4-tetrahydroquinolin-7-yl 4-methylphenyl carbamate 8b;
1-benzyl-1,2,3,4-tetrahydroquinolin-7-yl 2-fluorophenylcarbamate 8c;
1-benzyl-1,2,3,4-tetrahydroquinolin-7-yl 4-fluorophenylcarbamate 8d;
1-benzyl-1,2,3,4-tetrahydroquinolin-7-yl 2-chlorophenylcarbamate 8e;
1-benzyl-1,2,3,4-tetrahydroquinolin-7-yl 4-chlorophenylcarbamate 8f;
1-benzyl-1,2,3,4-tetrahydroquinolin-7-yl hexylcarbamate 8g;
1-benzyl-1,2,3,4-tetrahydroquinolin-7-yl heptylcarbamate 8h;
1-benzyl-1,2,3,4-tetrahydroquinolin-7-yl 2-methoxyphenylcarbamate 8i;
1-benzyl-1,2,3,4-tetrahydroquinolin-7-yl 4-methoxyphenylcarbamate 8j;
1-benzyl-1,2,3,4-tetrahydroquinolin-7-yl dimethylcarbamate 8k;
1-methyl-1,2,3,4-tetrahydroquinolin-7-yl 2-fluorophenylcarbamate 8l;
1,2,3,4-tetrahydroquinolin-7-yl 4-methylphenylcarbamate 9a;
1,2,3,4-tetrahydroquinolin-7-yl 2-fluorophenylcarbamate 9b;
1,2,3,4-tetrahydroquinolin-7-yl 4-fluorophenylcarbamate 9c;
1,2,3,4-tetrahydroquinolin-7-yl 4-chlorophenylcarbamate 9d;
1-(prop-2-ynyl)-1,2,3,4-tetrahydroquinolin-7-yl 2-methylphenylcarbamate 10a;
1-(prop-2-ynyl)-1,2,3,4-tetrahydroquinolin-7-yl heptylcarbamate 10b;
1-(prop-2-ynyl)-1,2,3,4-tetrahydroquinolin-7-yl 2-bromophenylcarbamate 10c;
1-(prop-2-ynyl)-1,2,3,4-tetrahydroquinolin-7-yl 2-isopropyl-6-methylphenylcarbamate 10d;
1-(prop-2-ynyl)-1,2,3,4-tetrahydroquinolin-7-yl 2-methoxyphenylcarbamate 10e;
1-(prop-2-ynyl)-1,2,3,4-tetrahydroquinolin-7-yl 4-chlorophenylcarbamate 10f;
1-(prop-2-ynyl)-1,2,3,4-tetrahydroquinolin-7-yl dimethylcarbamate 10g;
1-(prop-2-ynyl)-1,2,3,4-tetrahydroquinolin-7-yl diisopropylcarbamate 10h;

The structure of the representative compounds comprising:

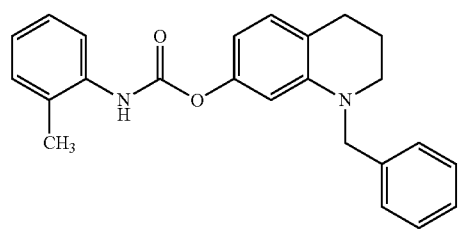 [SMILES: Cc1ccccc1NC(=O)Oc1ccc2c(c1)N(Cc1ccccc1)CCC2]

8a

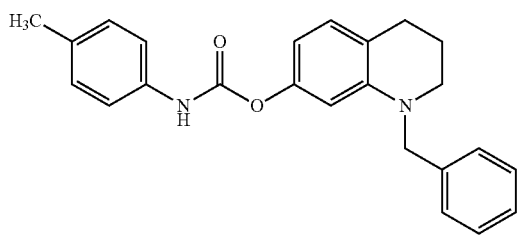 [SMILES: Cc1ccc(NC(=O)Oc2ccc3c(c2)N(Cc2ccccc2)CCC3)cc1]

8b

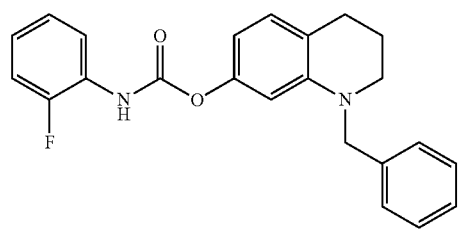

8c

8d
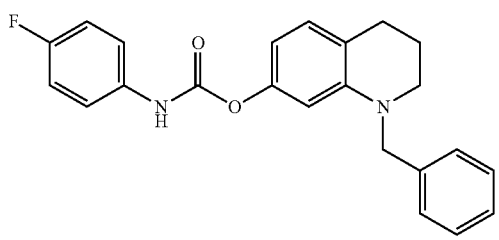
8e
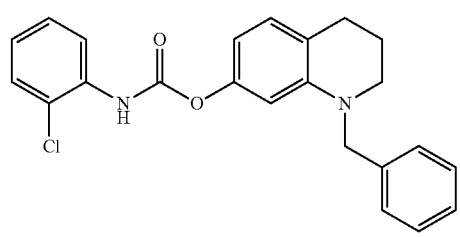 [SMILES: O=C(Nc1ccccc1F)Oc1ccc2c(c1)N(Cc1ccccc1)CCC2]
8f
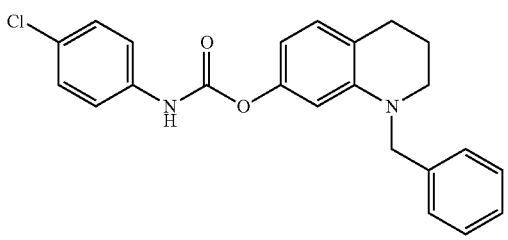 [SMILES: O=C(Nc1ccc(Cl)cc1)Oc1ccc2c(c1)N(Cc1ccccc1)CCC2]
8g
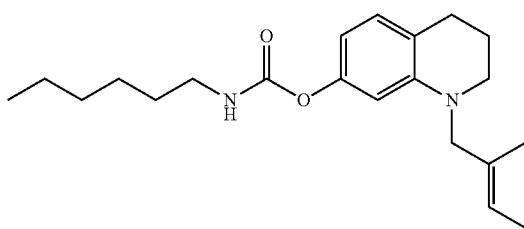
8h
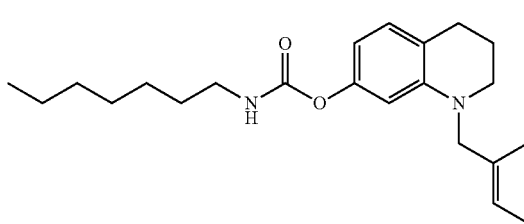
8i
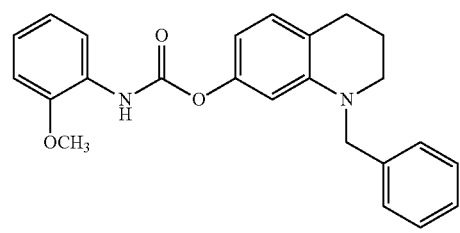 [SMILES: COc1ccccc1NC(=O)Oc1ccc2c(c1)N(Cc1ccccc1)CCC2]
8j
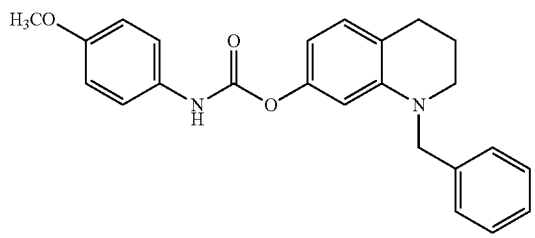 [SMILES: COc1ccc(NC(=O)Oc2ccc3c(c2)N(Cc2ccccc2)CCC3)cc1]
8k
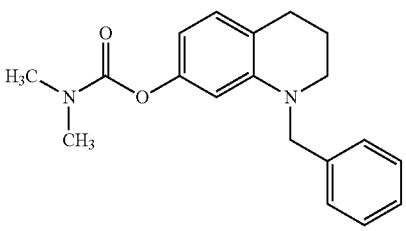 [SMILES: CN(C)C(=O)Oc1ccc2c(c1)N(Cc1ccccc1)CCC2]
8l
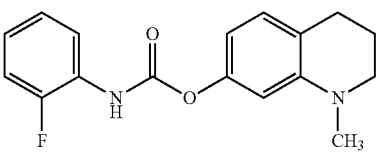 [SMILES: CN1CCCc2ccc(OC(=O)Nc3ccccc3F)cc21]
9a
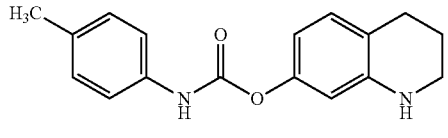 [SMILES: Cc1ccc(NC(=O)Oc2ccc3c(c2)NCCC3)cc1]
9b
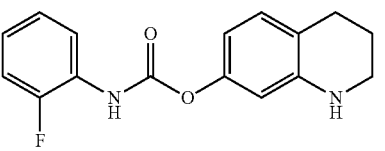 [SMILES: O=C(Nc1ccccc1F)Oc1ccc2c(c1)NCCC2]
9c
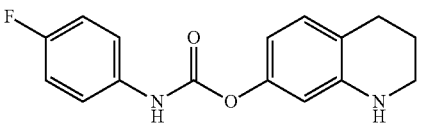 [SMILES: O=C(Nc1ccc(F)cc1)Oc1ccc2c(c1)NCCC2]
9d
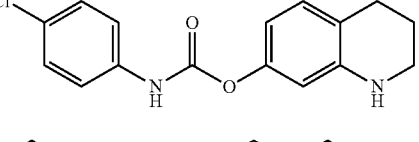
10a
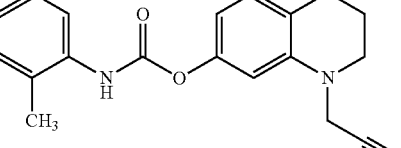
10b
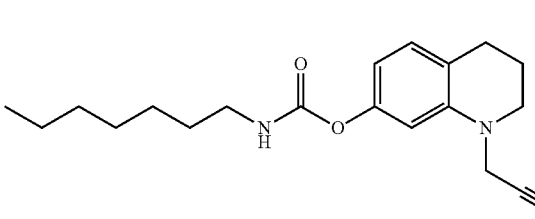

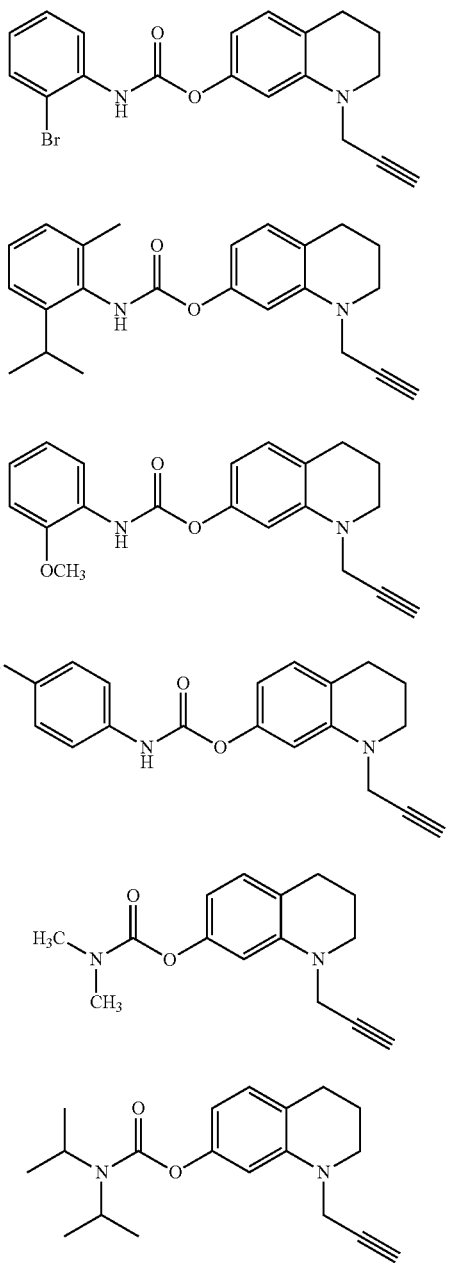

The compounds of the general formula A are useful as acetylcholinesterase (AChE) inhibitors for the treatment of Alzheimer's and other neurodegenerative disease.

Accordingly the present invention also provides a process for the preparation of compound of Formula A, wherein the process steps comprising a) mixing 1-substituted-1,2,3,4-tetrahydroquinolin-7-ol with a base and at least one organic solvent at a temperature in the range −10 to 60° C.;

b) stirring the mixture as obtained in step (a) under inert atmosphere for a period in the range 5 mins to 0.5 hrs;

c) adding substituted aryl or alkyl isocyanate or N,N-substituted alkyl carbamoyl halide to the mixture as obtained from step (b);

d) stirring the mixture as obtained in step (c) under inert atmosphere for a period in the range 3 to 72 hrs.;

e) extracting and purifying the substituted product to obtain the compounds 8a-k or 10a-g;

f) adding Pd—C 10% catalyst to the compounds 8b-d and 8f obtained from step (e) in the presence of a solvent by applying hydrogen pressure in the range of 50-60 psi for a period ranging between 4-12 hrs at a temperature ranging between 20 to 40° C. to obtain the compounds 9a-e;

In an embodiment of the invention wherein the base may be selected from organic or inorganic bases preferably from the group consisting of potassium carbonate, potassium iodide triethylamine and sodium hydride.

In another embodiment of the invention, wherein the organic solvent may be selected from the group consisting of tetrahydrofuran (THF), dichloromethane (DCM) and dimethylformamide (DMF).

In yet another embodiment of the present invention N,N-substituted alkyl carbamoyl halide is selected from the group consisting of N,N-dimethyl carbamoyl chloride and N,N-diisopropy carbamoyl chloride.

In an embodiment of the invention, wherein the nitrogen is used to create the inert atmosphere.

In still another embodiment of the invention, wherein substitution in isocyanate is selected from the group consisting of hexyl, heptyl, 2-chlorophenyl, 3-chlorophenyl, 4-chlorophenyl, 2-bromophenyl, 3-bromophenyl, 4-bromophenyl, 2-fluorophenyl, 4-fluorophenyl, 2-isopropyl, 2-methoxyphenyl, 4-methoxyphenyl, 2-methylphenyl, 3-methylphenyl, 4-methylphenyl, and 2-isopropyl-6-methylphenyl.

In a further embodiment of the invention, wherein the solvent used in step (f) is selected from the group consisting of ethanol and methanol.

In an embodiment, 1-substituted-1,2,3,4-tetrahydroquinolin-7-ol, substituents at 1st position are methyl, propargyl and benzyl.

In an embodiment of the invention, wherein compound of 8l can also be synthesized from 9b by reacting with methyl iodide in the presence of a base selected from a group consisting of potassium carbonate and potassium iodide in dimethylformamide as solvent and at a temperature ranging between −10 to 37° C. (Example 12: Method A and B)

In another embodiment of the invention, the reaction is carried out at a temperature in the range of −10° C. to 60° C. and for a period of three hours (hrs) to 72 hrs.

In another embodiment of the invention, where the range of room temperature is 20 to 40 degree C.

In yet another embodiment of the invention, the compound of formulae 9a-d are synthesized from 8b-e respectively using 10% Pd—C catalyst in a solvent selected from the group consisting of ethanol and methanol by applying hydrogen pressure in the range of 50-60 psi for a period of 4-10 hrs at the room temperature.

In another embodiment of the invention, the compound of formula 8l represented by formula A are synthesized from 9b by reacting with methyl iodide in the presence of bases potassium carbonate and potassium iodide in the dimethylformamide as solvent and at a temperature −10 to 37° C.

The present invention also comprises a method for the treatment of hypo-functioning of cholinergic system in a subject, comprising administering a pharmaceutically effective compound of formula A:

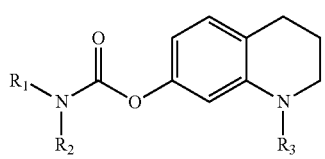

Formula A wherein R1 and R₂, is independently selected from the group consisting of hydrogen, saturated or unsaturated alkyl ($C_1$-$C_7$), aryl and, heteroaryl;

$R_3$ is selected from the group consisting of hydrogen, saturated or unsaturated alkyl (C1-C3), aralkyl such as benzyl, alkynyl such as propargyl.

In one embodiment of the invention, the hypo-functioning of the cholinergic system occurs in the peripheral or central nervous system of the subject.

In another embodiment of the invention, the subject is mammal.

BRIEF DESCRIPTION OF DRAWINGS

FIG. 1: represents Scheme of preparation of molecules of the present invention given wherein

ABBREVIATIONS

Figure 1:
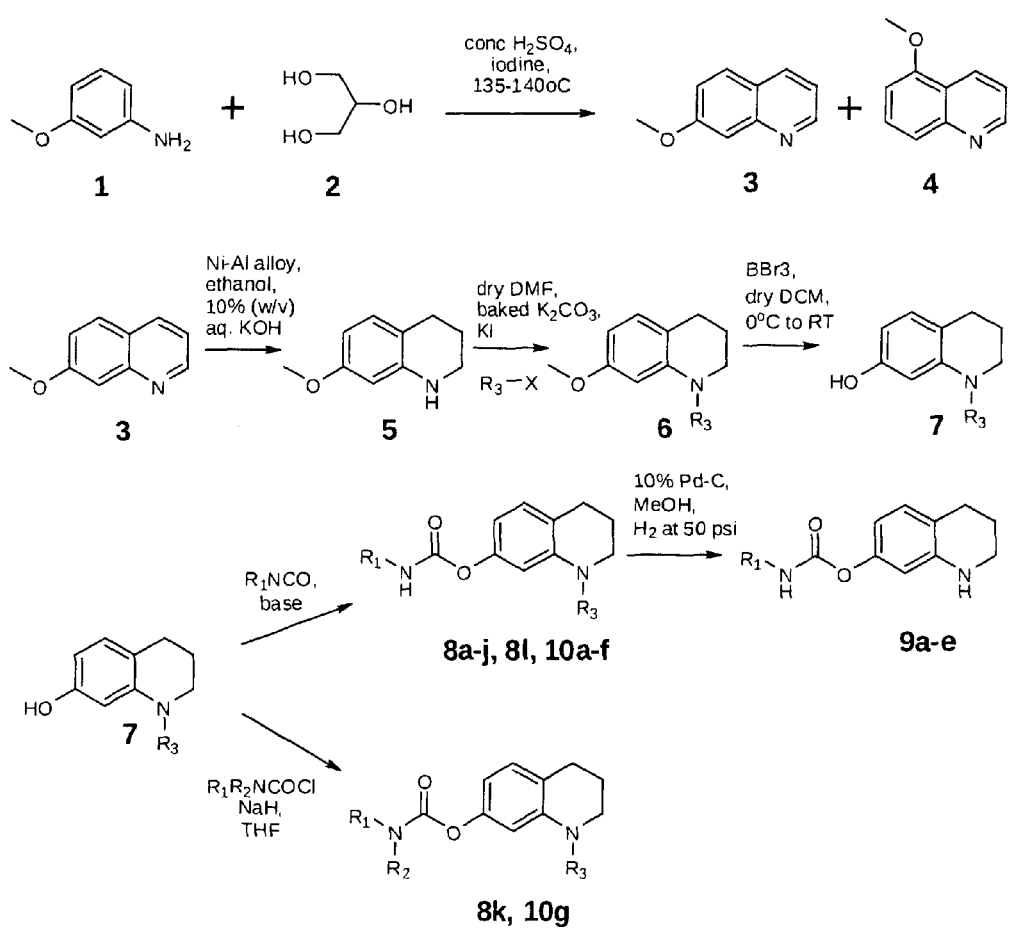

AChE: Acetylcholinesterase; AD: Alzheimer's disease; $BBr_3$: boron tribromide; DCM: dichloromethane; DMAP: NN-dimethylaminopyridine; DMF: dimethylformamide; EtOAc: ethyl acetate, EtOH: ethanol; IR: infra-red spectroscopy; MeOH: methanol, MS: mass spectroscopy; NMR: nuclear magnetic resonance, NN-DIPEA: N, N-diisopropyl-ethyl amine; RT: room temperature; THF: tetrahydrofuran; TLC: thin layer chromatographic.

DETAILED DESCRIPTION OF THE INVENTION

The main objects of the present invention are to:
provide novel cholinesterase inhibitors incorporating 1,2,3,4-tetrahydroquinoline flanked on one side by carbamate/carbamic acid ester and on the other side by hydrogen or alkyl like methyl, or alkynyl like propargyl or aralkyl like benzyl groups that exhibit better therapeutic efficacy to treat neurodegenerative diseases, particularly Alzheimer's disease or senile dementia.
provide a method for the treatment of Alzheimer's disease.
provide molecules useful for the treatment or prevention of senile dementia of Alzheimer's type.
provide molecules useful for the treatment or prevention of cerebral dementia.
provide molecules useful for the treatment or prevention of vascular dementia.
provide molecules useful for the treatment or prevention of alcoholic dementia.
provide molecules useful for the treatment or prevention of dementia associated with neurological disorders like epilepsy, neoplasm, post-trauma etc
provide compounds useful for the treatment or management or prevention of atony of the smooth muscle of the intestinal tract (paralytic ileus) and atony of the urinary bladder.
provide compounds useful for the treatment or prevention of glaucoma or myasthenia gravis.
provide compounds useful for the treatment or management or prevention of dementia related with behavioral disorders like depression, psychosis etc.

The above objects of the invention are achieved by novel pharmacologically active substances specifically substituted 1,2,3,4-tetrahydroquinolin-7-yl carbamates represented by formula A:

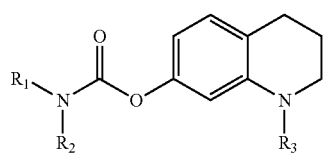

Formula A wherein R1 and R₂, independently selected from the group consisting of hydrogen, saturated or unsaturated alkyl ($C_1$-$C_7$), aryl and, heteroaryl;

$R_3$ is selected from the group consisting of hydrogen, saturated or unsaturated alkyl (C1-C3), aralkyl such as benzyl, alkynyl such as propargyl.

The representative compounds of formula A include:
8a. 1-benzyl-1,2,3,4-tetrahydroquinolin-7-yl 2-methylphenylcarbamate
8b. 1-benzyl-1,2,3,4-tetrahydroquinolin-7-yl 4-methylphenylcarbamate
8c. 1-benzyl-1,2,3,4-tetrahydroquinolin-7-yl 2-fluorophenylcarbamate
8d. 1-benzyl-1,2,3,4-tetrahydroquinolin-7-yl 4-fluorophenylcarbamate
8e. 1-benzyl-1,2,3,4-tetrahydroquinolin-7-yl 2-chlorophenylcarbamate
8f. 1-benzyl-1,2,3,4-tetrahydroquinolin-7-yl 4-chlorophenylcarbamate
8g. 1-benzyl-1,2,3,4-tetrahydroquinolin-7-yl hexylcarbamate
8h. 1-benzyl-1,2,3,4-tetrahydroquinolin-7-yl heptylcarbamate
8i. 1-benzyl-1,2,3,4-tetrahydroquinolin-7-yl 2-methoxyphenylcarbamate
8j. 1-benzyl-1,2,3,4-tetrahydroquinolin-7-yl 4-methoxyphenylcarbamate
8k. 1-benzyl-1,2,3,4-tetrahydroquinolin-7-yl dimethylcarbamate
8l. 1-methyl-1,2,3,4-tetrahydroquinolin-7-yl 2-fluorophenylcarbamate
9a. 1,2,3,4-tetrahydroquinolin-7-yl 4-methylphenylcarbamate
9b. 1,2,3,4-tetrahydroquinolin-7-yl 2-fluorophenylcarbamate
9c. 1,2,3,4-tetrahydroquinolin-7-yl 4-fluorophenylcarbamate
9d. 1,2,3,4-tetrahydroquinolin-7-yl 4-chlorophenylcarbamate
10a. 1-(prop-2-ynyl)-1,2,3,4-tetrahydroquinolin-7-yl 2-methylphenylcarbamate
10b. 1-(prop-2-ynyl)-1,2,3,4-tetrahydroquinolin-7-yl heptylcarbamate 10c. 1-(prop-2-ynyl)-1,2,3,4-tetrahydroquinolin-7-yl 2-bromophenylcarbamate 10d. 1-(prop-2-ynyl)-1,2,3,4-tetrahydroquinolin-7-yl 2-isopropyl-6-methylphenylcarbamate 10e. 1-(prop-2-ynyl)-1,2,3,4-tetrahydroquinolin-7-yl 2-methoxyphenylcarbamate 10f. 1-(prop-2-ynyl)-1,2,3,4-tetrahydroquinolin-7-yl 4-chlorophenylcarbamate 10g. 1-(prop-2-ynyl)-1,2,3,4-tetrahydroquinolin-7-yl dimethylcarbamate 10h. 1-(prop-2-ynyl)-1,2,3,4-tetrahydroquinolin-7-yl diisopropylcarbamate The preparation of the above representative compounds of formula A is outlined in Scheme 1. The synthesis of 7-methoxyquinoline (3) was carried out using Skraup's synthesis where meta-anisidine and glycerol were refluxed in the presence of sulphuric acid and iodine at 135-140° C. In this reaction, apart from 7-methoxyquinoline, one more positional isomer named 5-methoxy quinoline was formed in low yield. These two positional isomers 3 and 4 were separated using column chromatographic or salt formation techniques.

The methods for the synthesis of analogues of following intermediates namely 5, 6, and 7 are reported by us in the very recent past. (J. Med. Chem., 2010, 53 (17), 6490-6505).

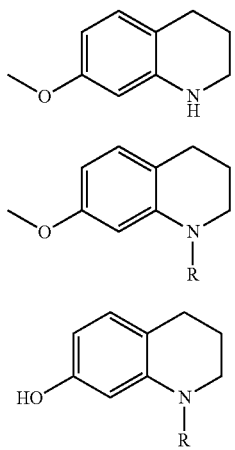

5

6

7

Carbamoylation of the intermediate 7 was accomplished using methods which are as following:

The synthesis of compounds 8a-k represented by formula A comprising reaction of substituted 1,2,3,4-tetrahydroquinolin-7-ol with substituted or unsubstituted aryl or alkyl isocyanate in the presence of a base and at least one organic solvent using a base to afford the corresponding compound represented by formula A.

The synthesis of compounds 10a-g represented by formula A comprising reaction of substituted 1,2,3,4-tetrahydroquinolin-7-ol with N,N-substituted alkyl carbamoyl halide in the presence of a base and at least one organic solvent using a base to afford the corresponding compound represented by formula A.

The synthesis of the compounds 9a-e of formulae A was done from 8b-d and 8f using 10% Pd—C catalyst in a solvent selected from the group consisting of methanol and ethanol by applying hydrogen pressure in the range of 50-60 psi for a period of 4-12 hrs at the room temperature.

Alternatively, the synthesis of compound of formula 8l represented by formula A can be done from 9b by reacting with methyl iodide in the presence of bases potassium carbonate and potassium iodide in the dimethylformamide as solvent and at a temperature −10 to 37° C.

The present invention also provides a pharmaceutical composition comprising therapeutically effective amount of a compound of general formula A, optionally along with one or more pharmaceutically acceptable carriers, additives, lubricants and diluents.

The following examples are given below to illustrate the details of the invention and should not be construed to limit the scope of the present invention.

Example 1

1-benzyl-1,2,3,4-tetrahydroquinolin-7-yl 2-methylphenylcarbamate (8a)

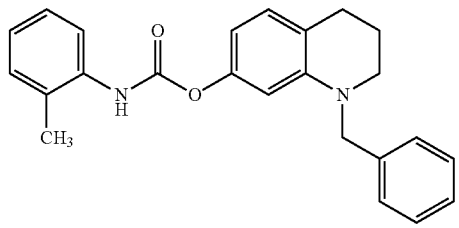

A mixture of 1-benzyl-1,2,3,4-tetrahydroquinolin-7-ol (550 mg, 2.30 mM) and triethylamine (0.4 mL) in dry dichloromethane (DCM, 10 mL) was stirred for half an hour under nitrogen atmosphere at room temperature (35° C.). To the stirred reaction mixture, o-tolyl isocyanate (428 mg/ml, 3.45 mM) was added at once and then the reaction mixture was further stirred for 72 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chloroform-hexane (1:9) to give 8a as colorless oil. Yield: 700 mg, 81.78%.

M.W. 372; Chemical Formula: $C_{24}H_{24}N_2O_2$; $^1$H-NMR (CDCl$_3$, 300 MHz). δ10.69 (bs, NH), 7.93-7.87 (d, 1H), 7.46-7.42 (dd, 2H), 7.29-7.25 (dd, 2H), 7.17-7.09 (m, 5H), 6.93-6.89 (d, 2H), 5.30 (s, 2H), 3.37-3.31 (t, J=8.355 Hz, 2H), 2.81-2.75 (t, 9.300 Hz, 2H), 2.147 (s, 3H), 2.06-1.99 (m, 2H). IR 3405, 2945, 2819, 2366, 1676, 1598, 1498, 1441, 1351, 1246, 1157, 972, 771, 692. FABMS: m/z: 373 (M+1)$^+$ Example 2

1-benzyl-1,2,3,4-tetrahydroquinolin-7-yl 4-methylphenylcarbamate (8b)

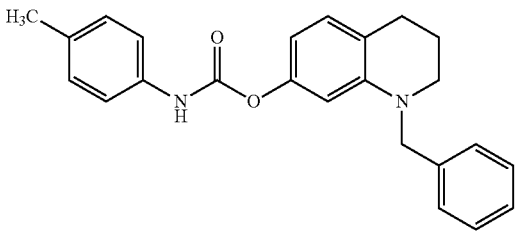

A mixture of 1-benzyl-1,2,3,4-tetrahydroquinolin-7-ol (824 mg, 3.44 mM) and triethylamine (0.6 mL) in dry tetrahydrofuran (THF, 5 ml) was stirred for half an hour under nitrogen atmosphere at room temperature (35° C.). To the stirred reaction mixture, p-tolyl isocyanate (651 mg/ml, 5.16 mM) was added at once and then the reaction mixture was further stirred for 72 hours under $N_2$ atmosphere at RT. The reaction mixture was concentrated under vacuum and then was quenched with distilled water followed by the extraction with chloroform (3×15 mL). The combined fractions of chloroform was again washed with water and dried over sodium sulphate. Further concentration of chloroform fraction under vacuum afforded the crude product, which was finally crystallized with methanol-ether (1:5) to give 8b as solid. Yield: 1.023 g, 79.77%.

M.W. 372; Chemical Formula: $C_{24}H_{24}N_2O_2$; m.p. 98° C.; $^1$H-NMR (CDCl$_3$, 300 Hz). □10.58 (bs, NH), 7.59-7.79 (d, 1H), 7.52-7.48 (d, 2H), 7.28-7.21 (dd, 2H), 7.14-7.03 (m, 5H), 6.86-6.79 (d, 2H), 5.18 (s, 2H), 3.32-3.26 (t, J=8.351 Hz, 2H), 2.80-2.73 (t, J=9.265 Hz, 2H), 2.146 (s, 3H), 2.05-1.99 (m, 2H). IR (KBr, cm$^{-1}$): 3403, 2965, 2839, 2366, 1686, 1600, 1496, 1348, 1239, 1157, 998, 762, 686. FABMS: m/z: 373 (M+1)$^+$ Example 3

1-benzyl-1,2,3,4-tetrahydroquinolin-7-yl 2-fluorophenylcarbamate (8c)

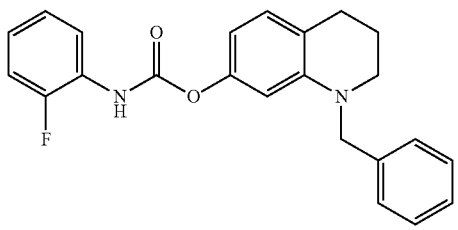

A mixture of 1-benzyl-1,2,3,4-tetrahydroquinolin-7-ol (805 mg, 3.36 mM) and triethylamine (0.6 mL) in dry tetrahydrofuran (THF, 5 ml) was stirred for half an hour under nitrogen atmosphere at room temperature (35° C.). To the stirred reaction mixture, 2-fluorophenyl isocyanate (565 mg/ml, 5.04 mM) was added at once and then the reaction mixture was further stirred for 72 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chloroform-hexane (1:9) to give 8c as oil. Yield: 1.02 g, 80.56%.

M.W. 376; Chemical Formula: $C_{23}H_{21}FN_2O_2$; $^1$H-NMR (CDCl$_3$, 200 MHz). □8.06-8.03 (d, 1H), 7.25-7.19 (m, 5H), 7.07-7.04 (d, 1H), 7.00 (s, 1H), 6.96-6.87 (m, 2H), 6.35-6.31 (d, 1H), 6.22 (s, 1H), 4.39 (s, 2H), 3.31-3.25 (t, J=5.460 Hz, 2H), 2.76-2.70 (m, 2H), 1.96-1.90 (t, J=5.575 Hz, 2H). IR (Neat, cm$^{-1}$): 3653, 3303, 2826, 2370, 2341, 1850, 1598, 1495, 1456, 1354, 1258, 1202, 1106, 1060, 847, 755, 654. FABMS: m/z: 377 (M+1)$^+$ Example 4

1-benzyl-1,2,3,4-tetrahydroquinolin-7-yl 4-fluorophenylcarbamate (8d)

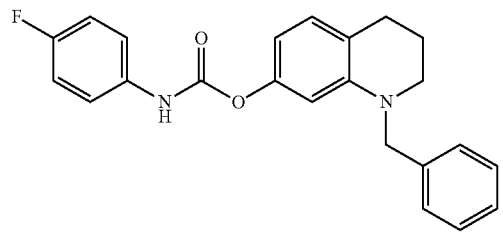

A mixture of 1-benzyl-1,2,3,4-tetrahydroquinolin-7-ol (800 mg, 3.34 mM) and triethylamine (0.5 mL) in dry tetrahydrofuran (THF, 5 ml) was stirred for half an hour under nitrogen atmosphere at room temperature (35° C.). To the stirred reaction mixture, 4-fluorophenyl isocyanate (570 mg/ml, 5.01 mM) was added at once and then the reaction mixture was further stirred for 72 hours under $N_2$ atmosphere at RT. The reaction mixture was concentrated under vacuum and then was quenched with distilled water (1 mL) followed by the extraction with chloroform (3×15 mL). The combined fractions of chloroform was again washed with water and dried over sodium sulphate. Further concentration of chloroform fraction under vacuum afforded the crude product, which was cystallize with methanol-ether (1:5) to yield 8d as solid. Yield: 1.06 g, 84.23%.

M.W. 376; Chemical Formula: $C_{23}H_{21}FN_2O_2$; m.p. 130° C.; $^1$H-NMR (CDCl$_3$, 200 MHz). □7.41-7.28 (m, 5H), 7.04-6.96 (t, J=5.684 Hz, 2H), 6.82-6.71 (m, 3H), 6.45-6.41 (d, 2H), 4.46 (s, 2H), 3.38-3.33 (t, J=5.456 Hz, 2H), 2.84-2.78 (t, J=5.568 Hz, 2H), 2.07-2.01 (m, 2H). IR (KBr, cm$^{-1}$): 3754, 3293, 3156, 3082, 3025, 2928, 2856, 2365, 1887, 1816, 1711, 1610, 1552, 1504, 1448, 1407, 1352, 1313, 1226, 1161, 1103, 1020, 969, 839, 798, 733, 691, 606, 581, 507, 456. FABMS: m/z: 377 (M+1)$^+$ Example 5

1-benzyl-1,2,3,4-tetrahydroquinolin-7-yl 2-chlorophenylcarbamate (8e)

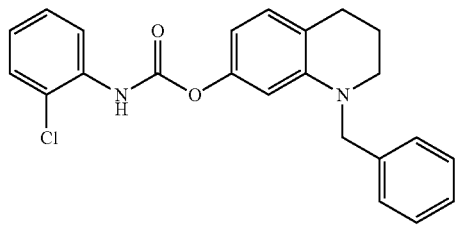

A mixture of 1-benzyl-1,2,3,4-tetrahydroquinolin-7-ol (800 mg, 3.34 mM) and triethylamine (0.6 mL) in dry tetrahydrofuran (THF, 5 ml) was stirred for half an hour under nitrogen atmosphere at room temperature (35° C.). To the stirred reaction mixture, 2-chlorophenyl isocyanate (604 mg/ml, 5.01 mM) was added at once and then the reaction mixture was further stirred for 62 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chloroform-hexane (1:9) to give 8e. Yield: 1.02 g, 77.66%.

M.W. 393; Chemical Formula: $C_{23}H_{21}ClN_2O_2$; m.p. 145° C.; $^1$H-NMR (CDCl$_3$, 200 MHz). □7.29-7.17 (m, 5H), 7.07-7.05 (d, 2H), 7.00 (s, 1H), 6.91-6.87 (d, 2H), 6.33-6.29 (d, 1H), 6.20 (s, 1H), 4.68 (s, 2H), 3.30-3.25 (t, J=5.460 Hz, 2H), 2.75-2.69 (m, 2H), 1.96-1.90 (t, J=5.670 Hz, 2H). IR 3677, 3291, 2928, 2364, 2340, 1756, 1647, 1591, 1552, 1476, 1441, 1386, 1352, 1294, 1232, 1197, 1163, 1054, 752, 687, 653, 555. FABMS: m/z: 393 (M)$^+$

Example 6

1-benzyl-1,2,3,4-tetrahydroquinolin-7-yl 4-chlorophenylcarbamate (8f)

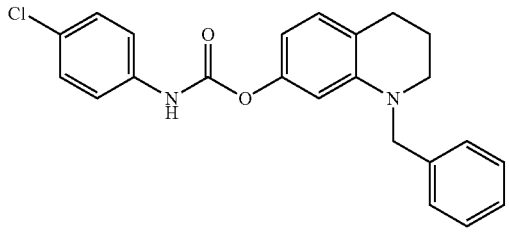

A mixture of 1-benzyl-1,2,3,4-tetrahydroquinolin-7-ol (800 mg, 3.34 mM) and triethylamine (1.5 mL) in dry tetrahydrofuran (THF, 5 ml) was stirred for half an hour under nitrogen atmosphere at room temperature (35° C.). To the stirred reaction mixture, 4-chlorophenyl isocyanate (641 mg/ml, 5.01 mM) was added at once and then the reaction mixture was further stirred for 72 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally crystallized with methanol-ether (1:6) to give 8f as solid. Yield: 1.06 g, 80.70%.

M.W. 393; Chemical Formula: $C_{23}H_{21}ClN_2O_2$; m.p. 120° C.; $^1$H-NMR (CDCl$_3$, 200 MHz). □7.38-7.27 (d, 5H), 6.96 (s, 1H), 6.78 (s, 2H), 6.76-6.72 (m, 3H), 6.45-6.41 (d, 2H), 4.46 (s, 2H), 3.38-3.33 (t, J=5.442 Hz, 2H), 2.83-2.77 (t, J=6.027 Hz, 2H), 2.03-1.97 (m, 2H). IR (KBr, cm$^{-1}$): 3332, 3106, 3033, 2929, 2844, 2367, 2228, 1718, 1601, 1542, 1507, 1452, 1399, 1349, 1308, 1220, 1195, 1012 826, 691, 614, 560, 505. FABMS: m/z: 393 (M)$^+$

Example 7

1-benzyl-1,2,3,4-tetrahydroquinolin-7-yl hexylcarbamate (8g)

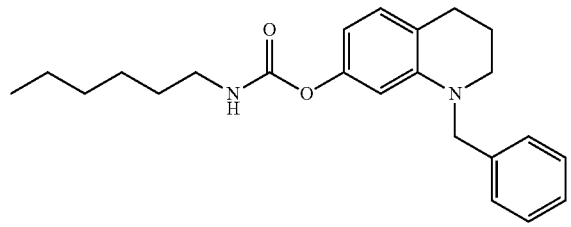

A mixture of 1-benzyl-1,2,3,4-tetrahydroquinolin-7-ol (500 mg, 2.09 mM) and triethylamine (0.4 mL) in dry tetrahydrofuran (THF, 5 ml) was stirred for half an hour under nitrogen atmosphere at room temperature (35° C.). To the stirred reaction mixture, n-hexyl isocyanate (457 mg/ml, 3.14 mM) was added at once and then the reaction mixture was further stirred for 72 hours under $N_2$ atmosphere a RT. The reaction mixture was concentrated under vacuum and then was added distilled water (15 ml) followed by the extraction with ether (3×15 mL). The ether layer was dried over sodium sulphate and concentrated under vacuum to afford the crude product, which was finally chromatographed using chloroform-hexane (1:9) to give 8g as solid. Yield: 0.619 g, 81%.

M.W. 366; Chemical Formula: $C_{23}H_{30}N_2O_2$; m.p. 85° C.; $^1$H-NMR (CDCl$_3$, 200 MHz). □7.35-7.26 (m 5H), 6.94-6.90 (d, 1H), 6.36-6.24 (d, 2H), 4.84 (bs, 1H), 4.45 (s, 2H), 3.34-3.29 (t, J=5.671 Hz 2H), 3.24-3.18 (m, 2H), 2.80-2.74 (t, J=6.225 Hz, 2H), 2.00-1.95 (t, J=5.825 Hz, 2H), 1.54-1.47 (m, 2H), 1.17 (m, 6H), 0.88-0.84 (t, J=6.343 Hz, 3H). IR (KBr, cm$^{-1}$): 3454, 3025, 2925, 2862 2350, 1724, 1616, 1509, 1462, 1362, 1222, 1178, 1022, 765, 668, 578. FABMS: m/z: 366 (M)$^+$

Example 8

1-benzyl-1,2,3,4-tetrahydroquinolin-7-yl heptylcarbamate (8h)

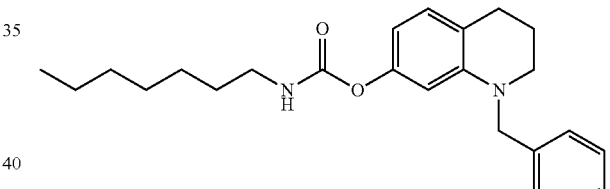

A mixture of 1-benzyl-1,2,3,4-tetrahydroquinolin-7-ol (500 mg, 2.09 mM) and triethylamine in dry tetrahydrofuran (THF, 5 ml) was stirred for half an hour under nitrogen atmosphere at room temperature (35° C.). To the stirred reaction mixture, n-heptyl isocyanate (505 mg/ml, 3.14 mM) was added at once and then the reaction mixture was further stirred for 72 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chloroform-hexane (1:9) to give 8h as solid. Yield: 0.600 g, 75.6%.

M.W. 380; Chemical Formula: $C_{24}H_{32}N_2O_2$; m.p. 50° C.; $^1$H-NMR (CDCl$_3$, 200 MHz). □7.18-7.09 (m, 5H), 6.78-6.74 (d, 1H), 6.22-6.11 (d, 2H), 4.81 (bs, 1H), 4.33 (s, 2H), 3.24-3.19 (t, J=5.619 Hz, 2H), 3.09-3.00 (m, 2H), 2.71-2.65 (t, J=6.214 Hz, 2H), 2.03-1.87 (m, 2H), 1.42-1.26 (m, 2H), 1.17 (m, 8H), 0.84-0.78 (t, J=6.191 Hz, 3H). IR (KBr, cm$^{-1}$): 3450, 3015, 2930, 2859, 2363, 2340, 1723, 1616, 1507, 1462, 1355, 1219, 1173, 1026, 769, 670. FABMS: m/z: 380 (M)$^+$

Example 9

1-benzyl-1,2,3,4-tetrahydroquinolin-7-yl 2-methoxyphenylcarbamate (8i)

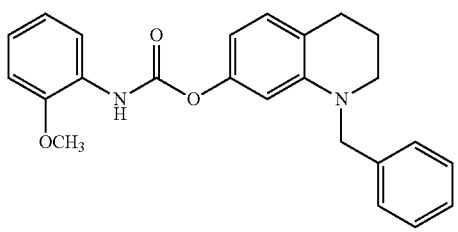

A mixture of 1-benzyl-1,2,3,4-tetrahydroquinolin-7-ol (500 mg, 2.09 mM) and triethylamine in dry tetrahydrofuran (THF, 5 ml) was stirred for half an hour under nitrogen atmosphere at room temperature (35° C.). To the stirred reaction mixture, 2-methoxyphenyl isocyanate (417 mg/ml, 3.14 mM) was added at once and then the reaction mixture was further stirred for 72 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chloroform-hexane (1:9) to give 8i as solid. Yield: 0.623 g, 76.85%.

M.W. 388; Chemical Formula: $C_{24}H_{24}N_2O_3$; m.p. 125° C.; $^1$H-NMR (CDCl$_3$, 200 MHz). □8.02-7.98 (d, 1H), 7.38 (s, 1H), 7.28-7.24 (m, 5H), 7.21 (s, 1H), 7.19 (s, 2H), 6.89-6.76 (d, 2H), 6.35-6.31 (d, 1H), 6.23 (s, 1H), 4.39 (s, 2H), 3.80 (s, 3H), 3.30-3.25 (t, J=5.403 Hz, 2H), 2.76-2.70 (m, 2H), 1.96-1.91 (t, J=5.608 Hz, 2H). IR (KBr, cm$^{-1}$): 3430, 2927, 2834, 2366, 1743, 1600, 1542, 1508, 1461, 1351, 1255, 1206, 1165, 1116, 1006, 970, 737, 572. FABMS: m/z: 389 (M+1)$^+$

Example 10

1-benzyl-1,2,3,4-tetrahydroquinolin-7-yl 4-methoxyphenylcarbamate (8j)

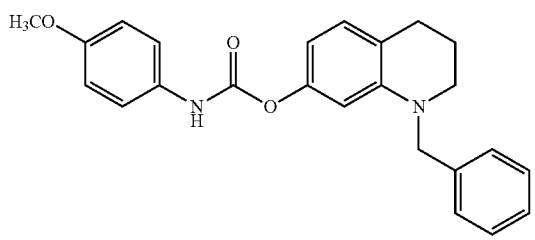

A mixture of 1-benzyl-1,2,3,4-tetrahydroquinolin-7-ol (500 mg, 2.09 mM) and triethylamine in dry tetrahydrofuran (THF, 5 ml) was stirred for half an hour under nitrogen atmosphere at room temperature (35° C.). To the stirred reaction mixture, 4-methoxyphenyl isocyanate (407 mg/ml, 3.14 mM) was added at once and then the reaction mixture was further stirred for 72 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chlorophorm-hexane (1:9) to give 8j as solid. Yield: 0.588 g, 72.53%.

M.W. 388; Chemical Formula: $C_{24}H_{24}N_2O_3$; m.p. 170° C.; $^1$H-NMR (CDCl$_3$, 200 MHz). □7.18-7.16 (d, 5H), 6.74-6.69 (d, 2H), 6.62 (s, 1H), 6.36-6.31 (d, 2H); 4.36 (s, 2H), 3.68 (s, 3H), 3.29-3.23 (t, J=5.341 Hz, 2H), 2.75-2.69 (m, 2H), 1.96-1.90 (t, J=5.467 Hz, 2H). IR (KBr, cm$^{-1}$): 3346, 2933, 2832, 2369, 2341, 1873, 1709, 1600, 1509, 1445, 1351, 1239, 1174, 1116, 1015, 861, 823, 725, 645, 520. FABMS: m/z: 389 (M+1)$^+$

Example 11

1-benzyl-1,2,3,4-tetrahydroquinolin-7-yl dimethylcarbamate (8k)

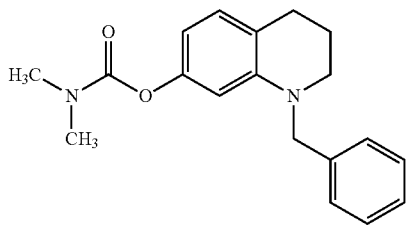

A solution of 1-benzyl-1,2,3,4-tetrahydroquinolin-7-ol (500 mg, 2.09 mM) in dry tetrahydrofuran (THF, 8 ml) was added to the stirred solution of sodium hydride in dry THF at −10° C. during 5 minutes under nitrogen environment. The reaction mixture was stirred for 30 minutes. Then, N,N-dimethyl carbamoyl chloride (265 mg/ml, 3.14 mM) was added to the stirring reaction mixture. The mixture was stirred further for 7 hours during which the temperature was allowed to reach the room temperature (35° C.). The reaction mixture was diluted with ethyl acetate, washed with water, and dried over sodium sulphate. The combined fractions of ethyl acetate were concentrated under vacuum and chromatographed using ethyl acetate:hexane (1:49) to afford 8k as solid. Yield: 0.796 g, 76.19%.

M.W. 310; Chemical Formula: $C_{19}H_{22}N_2O_2$; m.p. 104° C.; $^1$H-NMR (CDCl$_3$, 300 MHz). □7.33-7.21 (m, 6H), 6.93-6.90 (d, 1H), 6.33-6.25 (m, 2H), 4.45 (s, 2H), 3.31-3.28 (t, J=5.670 Hz, 2H), 3.00 (s, 6H), 2.79-2.75 (t, J=6.205 Hz, 2H), 2.01-1.93 (m, 2H). IR (KBr, cm$^{-1}$): 3019, 2930, 2856, 2402, 1712, 1611, 1506, 1446, 1389, 1216, 1179, 1030, 972, 931, 871, 761, 670. ESMS: 311 (M+1)$^+$

Example 12

1-methyl-1,2,3,4-tetrahydroquinolin-7-yl 2-fluorophenylcarbamate (8l)

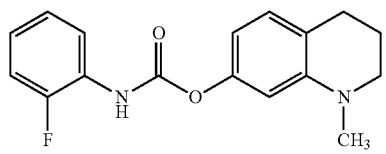

Method A:
A solution of 1-methyl-1,2,3,4-tetrahydroquinolin-7-ol (500 mg, 2.09 mM) in dry dimethylformamide (DMF, 5 mL)

was added to the stirred solution of sodium hydride in dry DMF at −10° C. during 5 minutes under nitrogen environment. The reaction mixture was stirred for 30 minutes. Then, 2-fluorophenyl isocyanate (352 mg/ml, 3.14 mM) was added to the stirring reaction mixture. The mixture was stirred further for 3 hours during which the temperature was allowed to reach the room temperature (37° C.). The reaction mixture was quenched with water, diluted with water, extracted with ethyl acetate and dried over sodium sulphate. The combined fractions of ethyl acetate were concentrated under vacuum and chromatographed using ethyl acetate:hexane (1:49) to afford the pure compound 8l as oil. Yield: 580 mg, 63.03%.

M.W. 300; Chemical Formula: $C_{17}H_{17}FN_2O_2$; $^1$H-NMR (CDCl$_3$, 200 MHz). □8.89 (bs, NH), 7.32-7.26 (d, 2H), 7.15-7.06 (d, 2H), 6.39-6.31 (d, 2H), 6.25-6.19 (d, 2H), 3.31-3.25 (t, J=5.505 Hz, 2H), 2.78-2.68 (t, 6.355 Hz, 2H), 2.02-1.88 (m, 2H). IR (Neat, cm$^{-1}$): 3415, 3296, 2924, 2866, 2348, 1905, 1715, 1604, 1555, 1515, 1408, 1362, 1325, 1232, 1117, 1018, 972, 724, 693, 512. FABMS: m/z: 301 (M+1)$^+$ Method B:

A solution of 1,2,3,4-tetrahydroquinolin-7-yl 2-fluorophenylcarbamate (300 mg, 1.84 mM) in dry dimethylformamide (DMF, 5 mL) was added to the stirred solution of sodium hydride in dry DMF at −10° C. during 5 minutes under nitrogen environment. The reaction mixture was stirred for 30 minutes. Then, methyl iodide (285 mg/ml, 2 mM), was added to the stirring reaction mixture. The mixture was stirred further for 3 hours during which the temperature was allowed to reach the room temperature (37° C.). The reaction mixture was quenched with water, diluted with water, extracted with ethyl acetate and dried over sodium sulphate. The combined fractions of ethyl acetate were concentrated under vacuum and chromatographed using ethyl acetate:hexane (1:49) to afford the pure compound 8l as oil. Yield: 300 mg, 54.33%.

Example 13

1,2,3,4-tetrahydroquinolin-7-yl 4-methylphenylcarbamate (9a)

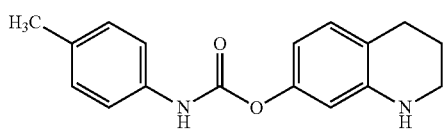

A nitrogen-flushed mixture of 1-benzyl-1,2,3,4-tetrahydroquinolin-7-yl p-tolylcarbamate (400 mg, 1.07 mM) and 5% Pd—C (0.2 g) in absolute ethanol (20 mL) was shaken in a parr apparatus at room temperature under 50 psi pressure of hydrogen for 10 hrs. Pd—C was then discarded through filtration through celite pad and the ethanol fraction was concentrated under vacuum and finally purified using column chromatography using chloroform-hexane (1:9) as eluent to afford 9a as solid. Yield: 255 mg, 84.11%.

M.W. 282; Chemical Formula: $C_{17}H_{18}N_2O_2$; m.p. 128° C.; $^1$H-NMR (CDCl$_3$, 200 MHz). □7.30-7.25 (d, 2H), 7.10-7.06 (d, 2H), 6.75 (s, 1H), 6.33-6.31 (d, 1H), 6.25-6.23 (d, 2H), 3.31-3.25 (t, J=5.485 Hz, 2H), 2.76-2.70 (t, 6.350 Hz, 2H), 1.95-1.86 (m, 2H). IR (KBr, cm$^{-1}$): 3404, 3296, 2922, 2855, 2371, 2341, 1893, 1709, 1601, 1546, 1507, 1439, 1405, 1351, 1319, 1231, 1163, 1117, 1013, 972, 828, 727, 694, 508. FABMS: m/z: 283 (M+1)$^+$ Example 14

1,2,3,4-tetrahydroquinolin-7-yl 2-fluorophenylcarbamate (9b)

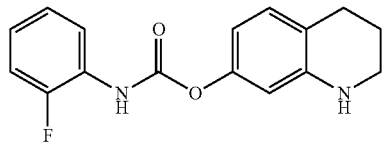

A nitrogen-flushed mixture of 1-benzyl-1,2,3,4-tetrahydroquinolin-7-yl 2-fluorophenylcarbamate (1.00 g, 2.66 mM) and 5% Pd—C (400 mg) in absolute ethanol was shaken in a parr apparatus at room temperature under 50 psi pressure of hydrogen for 8 hrs. Pd—C was then discarded through filtration through celite pad. The reaction mixture was concentrated under vacuum and then purified using column chromatography using silica as solid phase and chloroform-hexane (1:9) as eluent to afford 9b as oil. Yield: 650 mg, 85.46%.

M.W. 286; Chemical Formula: $C_{16}H_{15}FN_2O_2$; $^1$H-NMR (CDCl$_3$, 200 MHz). □8.22 (bs, NH), 7.26-7.22 (d, 2H), 7.14-7.11 (d, 1H), 7.06-7.01 (d, 2H), 6.96-6.92 (d, 3H), 3.31-3.28 (t, J=4.792 Hz, 2H), 2.77-2.71 (t, 6.054 Hz, 2H), 1.96-1.90 (m, 2H). IR (Neat, cm$^{-1}$): 3409, 2931, 2846, 2364, 2341, 1740, 1620, 1540, 1506, 1456, 1319, 1259, 1219, 1159, 1106, 936, 856, 810, 755, 670, 538, 484, 456. FABMS: m/z: 287 (M+1)$^+$ Example 15

1,2,3,4-tetrahydroquinolin-7-yl 4-fluorophenylcarbamate (9c)

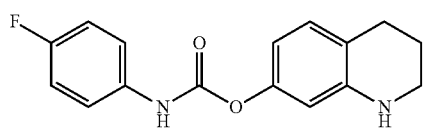

A nitrogen-flushed mixture of 1-benzyl-1,2,3,4-tetrahydroquinolin-7-yl 4-fluorophenylcarbamate (800 mg, 2.13 mM) and 5% Pd—C (200 mg) in absolute ethanol was shaken in a parr apparatus at room temperature under 50 psi pressure of hydrogen for 8 hrs. Pd—C was then discarded through filtration through celite pad. The reaction mixture was concentrated under vacuum and then purified using column chromatography using silica as solid phase and chloroform-hexane (1:9) as eluent to afford 9c as semisolid. Yield: 550 mg, 90.39%.

M.W. 286; Chemical Formula: $C_{16}H_{15}FN_2O_2$; $^1$H-NMR (CDCl$_3$, 200 MHz). □8.82 (bs, NH), 7.46-7.30 (d, 2H), 7.29-7.18 (d, 2H), 7.09-7.01 (d, 2H), 7.00-6.90 (d, 2H), 3.33-3.27 (t, J=4.823 Hz, 2H), 2.79-2.70 (t, 5.954 Hz, 2H), 2.06-1.89 (m, 2H). IR (Neat, cm$^{-1}$): 3427, 3307, 3155, 2951, 2927, 2839, 2366, 2344; 2241, 1885, 1717, 1613, 1507, 1441, 1408, 1356, 1272, 1159, 1099, 936, 834, 754, 690, 539, 514. FABMS: m/z: 287 (M+1)$^+$

Example 16

1,2,3,4-tetrahydroquinolin-7-yl 4-chlorophenylcarbamate (9d)

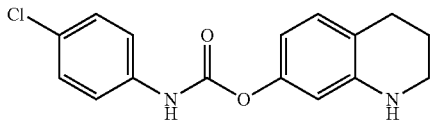 [SMILES: O=C(Nc1ccc(Cl)cc1)Oc1ccc2c(c1)NCCC2]

A nitrogen-flushed mixture of 1-benzyl-1,2,3,4-tetrahydroquinolin-7-yl 4-chlorophenylcarbamate (330 mg, 0.84 mM) and 5% Pd—C (60 mg) in absolute ethanol was shaken in a parr apparatus at room temperature under 50 psi pressure of hydrogen for 7 hrs. Pd—C was then discarded through filtration using celite pad. The ethanol fraction was concentrated under vacuum and then purified using column chromatography using silica as solid phase and chloroform-hexane (1:9) as eluent to afford 9d as crystalline white solid. Yield: 235 mg, 92.41%.

M.W. 302; Chemical Formula: $C_{16}H_{15}ClN_2O_2$; m.p. 118° C.; $^1$H-NMR (CDCl$_3$, 200 MHz). □8.86 (bs, NH), 7.51-7.30 (d, 2H), 7.32-7.23 (d, 2H), 7.09-7.00 (d, 2H), 6.98-6.85 (d, 2H), 3.31-3.22 (t, J=4.828 Hz, 2H), 2.79-2.69 (t, 5.961 Hz, 2H), 2.05-1.83 (m, 2H). IR (KBr, cm$^{-1}$): 3424, 3301, 3139, 2950, 2917, 2832, 2365, 1885, 1717, 1612, 1512, 1445, 1408, 1366, 1162, 1102, 934, 754, 690, 541, 522. FABMS: m/z: 303 (M+1)$^+$

Example 17

1-(prop-2-ynyl)-1,2,3,4-tetrahydroquinolin-7-yl 2-methylphenylcarbamate (10a)

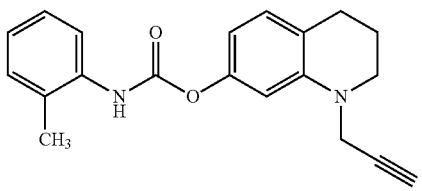 [SMILES: C#CCN1CCCc2ccc(OC(=O)Nc3ccccc3C)cc21]

A mixture of 1-(prop-2-ynyl)-1,2,3,4-tetrahydroquinolin-7-ol (250 mg, 1.34 mM) and triethylamine (0.2 mL) in dry tetrahydrofuran (THF, 5 mL) was stirred for half an hour under nitrogen atmosphere at room temperature (35° C.). To the stirred reaction mixture, o-tolyl isocyanate (250 mg/ml, 2.01 mM) was added at once and then the reaction mixture was further stirred for 48 hours under N$_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chlorophorm-hexane (1:19) to give 10a as solid. Yield: 300 mg, 70.13%.

M.W. 320; Chemical Formula: $C_{20}H_{20}N_2O_2$; m.p. 96° C.; $^1$H-NMR (CDCl$_3$, 300 MHz). □7.87-7.83 (d, 1H), 7.26 (s, 1H), 7.18-7.09 (d, 1H), 7.06-6.99 (m, 2H), 6.75-6.23 (m, 2H), 4.04-4.03 (d, 2H), 3.40-3.35 (t, J=8.565 Hz, 2H), 2.78-2.71 (t, J=9.60 Hz, 2H), 2.33 (s, 3H), 2.24 (s, 1H), 2.10-1.98 (m, 2H). IR (KBr, cm$^{-1}$): 3410, 3270, 3022, 2927, 2849, 2365, 2208, 2110, 1750, 1547, 1594, 1528, 1501, 1450, 1305, 1201, 1162, 1045, 961, 840, 759, 647, 571. ESMS: m/z: 321 (M+1)$^+$

Example 18

1-(prop-2-ynyl)-1,2,3,4-tetrahydroquinolin-7-yl heptylcarbamate (10b)

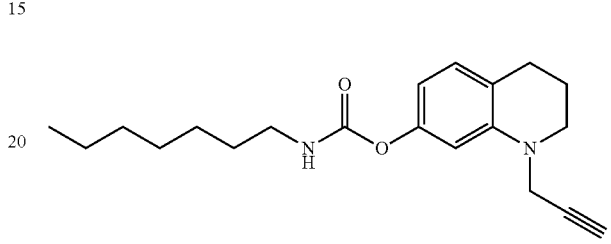

A mixture of 1-(prop-2-ynyl)-1,2,3,4-tetrahydroquinolin-7-ol (500 mg, 2.67 mM) and triethylamine (0.6 mL) in dry tetrahydrofuran (THF, 5 mL) was stirred for half an hour under nitrogen atmosphere at room temperature (35° C.). To the stirred reaction mixture, heptyl isocyanate (644 mg/ml, 4 mM) was added at once and then the reaction mixture was further stirred for 48 hours under N$_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chlorophorm-hexane (1:19) to get 10b as creamish solid. Yield: 625 mg, 71.26%.

M.W. 328; Chemical Formula: $C_{20}H_{28}N_2O_2$; m.p. 54° C.; $^1$H-NMR (CD$_3$OD, 300 MHz). □7.46 (s, NH), 6.93-6.90 (d, 1H), 6.46-6.39 (m, 2H), 3.99 (s, 2H), 3.31-3.27 (t, J=5.655 Hz, 2H), 3.22-3.18 (t, J=7.05 Hz, 2H), 2.75-2.71 (t, J=6.315 Hz, 2H), 2.26 (s, 1H), 2.03-1.95 (m, 2H), 1.56-1.48 (m, 2H), 1.33-1.27 (t, J=5.85 Hz, 10H), 0.90-0.87 (d, 3H). IR 3378, 3272, 3023, 2932, 2851, 2365, 2198, 2119, 1743, 1546, 1599, 1601, 1450, 1305, 1201, 1162, 1045, 961, 840, 759, 647, 571. ESMS: m/z: 329 (M+1)$^+$

Example 19

1-(prop-2-ynyl)-1,2,3,4-tetrahydroquinolin-7-yl 2-bromophenylcarbamate (10c)

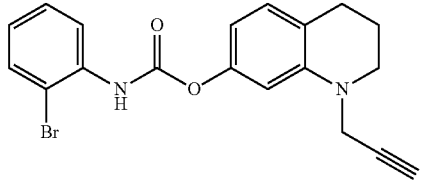 [SMILES: C#CCN1CCCc2ccc(OC(=O)Nc3ccccc3Br)cc21]

A mixture of 1-(prop-2-ynyl)-1,2,3,4-tetrahydroquinolin-7-ol (400 mg, 2.14 mM) and triethylamine (0.6 mL) in dry tetrahydrofuran (THF, 5 mL) was stirred for half an hour under nitrogen atmosphere at room temperature (35° C.). To the stirred reaction mixture, 2-bromophenyl isocyanate (396 mg/ml, 3.21 mM) was added at once and then the reaction mixture was further stirred for 36 hours under $N_2$ atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chlorophorm-hexane (1:19) to afford 10c as solid. Yield: 540 mg, 65.61%.

M.W. 385; Chemical Formula: $C_{19}H_{17}BrN_2O_2$; m.p. 105° C.; $^1$H-NMR (CDCl$_3$, 300 MHz). ☐9.39 (bs, 1H), 7.87-7.83 (d, 1H), 7.61-7.55 (d, 1H), 7.37-7.28 (m, 1H), 7.01-6.96 (m, 2H), 6.55-6.52 (m, 2H), 4.02 (s, 2H), 3.35-3.31 (t, J=5.68 Hz, 2H), 2.80-2.76 (t, J=6.34 Hz, 2H), 2.20 (s, 1H), 2.05-2.01 (m, 2H). IR (KBr, cm$^{-1}$): 3423, 3265, 3022, 2931, 2852, 2356, 2199, 1743, 1594, 1528, 1501, 1450, 1305, 1201, 1162, 1045, 969, 756, 652. ESMS: m/z: 386 (M+1)$^+$ Example 20

1-(prop-2-ynyl)-1,2,3,4-tetrahydroquinolin-7-yl 2-isopropyl-6-methylphenylcarbamate (10d)

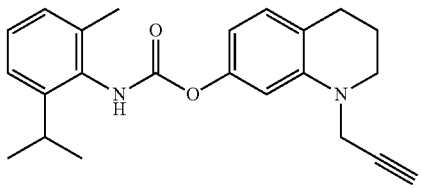 [SMILES: C#CCN1CCCc2ccc(OC(=O)Nc3c(C)cccc3C(C)C)cc21]

A mixture of 1-(prop-2-ynyl)-1,2,3,4-tetrahydroquinolin-7-ol (400 mg, 2.14 mM) and triethylamine (0.6 mL) in dry tetrahydrofuran (THF, 5 mL) was stirred for half an hour under nitrogen atmosphere at room temperature (35° C.). To the stirred reaction mixture, 2-isopropyl-6-methylphenyl isocyanate (558 mg/ml, 3.21 mM) was added at once and then the reaction mixture was further stirred for 30 hours under N2 atmosphere at RT. The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chloroform-hexane (1:19) to afford 10d as solid. Yield: 520 mg, 67.16%.

M.W. 362; Chemical Formula: $C_{23}H_{26}N_2O_2$; m.p. 120° C.; $^1$H-NMR (CDCl$_3$, 300 MHz). ☐7.28-7.22 (m, 2H), 7.14-7.12 (d, 1H), 6.99-6.96 (d, 1H), 6.58-6.54 (d, 1H), 6.39-6.33 (d, 1H), 4.02 (s, 2H), 3.40-3.20 (t, 4.22 Hz, 2H), 2.76-2.74 (t, J=5.68 Hz, 2H), 2.44-2.37 (t, J=6.41 Hz, 2h), 2.19 (s, 1H), 2.01-1.99 (m, 2H), 1.60 (s, 3H), 1.28-1.26 (d, 6H). ESMS: m/z: 363 (M+1)$^+$ Example 21

1-(prop-2-ynyl)-1,2,3,4-tetrahydroquinolin-7-yl 2-methoxyphenylcarbamate (10e)

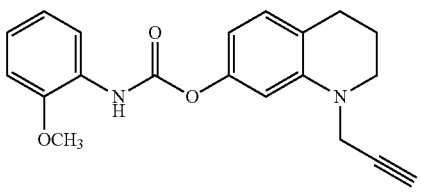 [SMILES: C#CCN1CCCc2ccc(OC(=O)Nc3ccccc3OC)cc21]

A mixture of 1-(prop-2-ynyl)-1,2,3,4-tetrahydroquinolin-7-ol (400 mg, 2.14 mM) and triethylamine (0.6 mL) in dry tetrahydrofuran (THF, 5 mL) was stirred for half an hour under nitrogen atmosphere at room temperature (35° C.). To the stirred reaction mixture, 2-methoxyphenyl isocyanate (427 mg/ml, 3.21 mM) was added at once and then the reaction mixture was further stirred for 48 hours under N2 atmosphere at RT (35° C.). The reaction mixture was concentrated under vacuum and then was added distilled water (15 mL) followed by the extraction with ether (3×15 mL). The ether layer was dried over sodium sulphate and concentrated under vacuum to afford the crude product (10e), which was finally chromatographed using chlorophorm-hexane (1:19) to give 10e as solid. Yield: 480 mg, 66.80%.

M.W. 336; Chemical Formula: $C_{20}H_{20}N_2O_3$; m.p. 83° C.; $^1$H-NMR (CDCl$_3$, 200 MHz). ☐8.02 (bs, 1H), 7.18 (s, 1H), 6.99-6.78 (m, 4H), 6.46-6.43 (d, 2H), 3.92 (s, 2H), 3.82 (s, 2H), 3.26-3.20 (t, J=5.73 Hz, 2H), 2.70-2.64 (t, J=6.38 Hz, 2H), 2.11 (s, 1H), 1.98-1.89 (m, 2H). IR (KBr, cm$^{-1}$): 3411, 3270, 3022, 2927, 2765, 2208, 2098, 1738, 1547, 1594, 1528, 1501, 1450, 1305, 1201, 1162, 1045, 961, 840, 759, 647, 571. ESMS: m/z: 337 (M+1)$^+$ Example 22

1-(prop-2-ynyl)-1,2,3,4-tetrahydroquinolin-7-yl 4-chlorophenylcarbamate (10f)

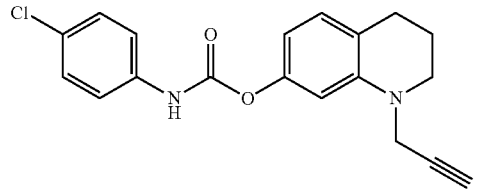 [SMILES: C#CCN1CCCc2ccc(OC(=O)Nc3ccc(Cl)cc3)cc21]

A mixture of 1-(prop-2-ynyl)-1,2,3,4-tetrahydroquinolin-7-ol (400 mg, 2.14 mM) and triethylamine (0.6 mL) in dry tetrahydrofuran (THF; 5 mL) was stirred for half an hour under nitrogen atmosphere at room temperature (35° C.). To the stirred reaction mixture, 4-chlorophenyl isocyanate (411 mg/ml, 3.21 mM) was added at once and then the reaction mixture was further stirred for 32 hours under $N_2$ atmosphere at RT (35° C.). The reaction mixture was concentrated under vacuum and then was added distilled water (15 mL) followed by the extraction with ether (3×15 mL). The ether layer was dried over sodium sulphate and concentrated under vacuum to afford the crude product, which was finally chromatographed using chlorophorm-hexane (1:19) to afford 10f as solid. Yield: 520 mg, 71.42%.

M.W. 340; Chemical Formula: $C_{19}H_{17}ClN_2O_2$; m.p. 160° C.; $^1$H-NMR (CDCl$_3$, 200 MHz). □8.86 (bs, NH), 7.51-7.30 (d, 2H), 7.32-7.23 (d, 2H), 7.09-7.00 (d, 2H), 6.98-6.85 (d, 2H), 4.02 (s, 2H), 3.35-3.31 (t, J=5.678 Hz, 2H), 2.80-2.76 (t, J=6.298 Hz, 2H), 2.20 (s, 1H), 2.10-1.98 (m, 2H). IR (KBr, cm$^{-1}$) 3410, 3270, 3022, 2927, 2849, 2365, 2208, 2112, 1745, 1547, 1594, 1528, 1501, 1450, 1309, 1201, 1055, 963, 844, 761, 653, 568. ESMS: m/z: 314 (M+1)$^+$ Example 23

1-(prop-2-ynyl)-1,2,3,4-tetrahydroquinolin-7-yl dimethylcarbamate (10g)

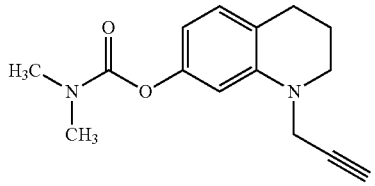 [SMILES: C#CCN1CCCc2ccc(OC(=O)N(C)C)cc21]

A solution of 1-(prop-2-ynyl)-1,2,3,4-tetrahydroquinolin-7-ol (400 mg, 2.14 mM) in dry tetrahydrofuran (THF; 5 mL) was added to the stirred solution of sodium hydride in dry THF at −10° C. during 5 minutes under nitrogen environment at room temperature (25° C.). The reaction mixture was stirred for 30 minutes. Then, N,N-dimethyl carbamoyl chloride (0.25 mL) was added to the stirring reaction mixture. The mixture was stirred further for 7 hours during which the temperature was allowed to reach the room temperature (35° C.). The reaction mixture was diluted with ethyl acetate, washed with water, and dried over sodium sulphate. The combined fractions of ethyl acetate were concentrated under vacuum and chromatographed using ethyl acetate:hexane (1:49) to afford 10g as solid. Yield: 414 mg, 75.6%.

M.W. 258; Chemical Formula: $C_{15}H_{18}N_2O_2$; m.p. 145° C.; $^1$H-NMR (CDCl$_3$, 300 MHz). □6.93-6.90 (d, 2H), 6.33 (s, 1H), 4.45 (s, 2H), 3.31-3.28 (t, J=5.674 Hz, 2H), 3.00 (s, 6H), 2.79-2.75 (t, J=6.201 Hz, 2H), 2.13 (s, 1H), 2.01-1.93 (m, 2H). IR (KBr, cm$^{-1}$) 3019, 2935, 2858, 2422, 1713, 1621, 1448, 1382, 1216, 1179, 1030, 972, 956, 760, 675. ESMS: m/z: 259 (M+1)$^+$ Example 24

1-(prop-2-ynyl)-1,2,3,4-tetrahydroquinolin-7-yl diisopropylcarbamate (10h)

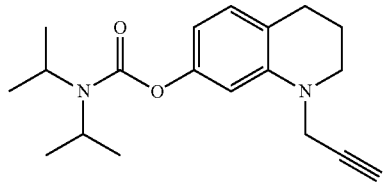 [SMILES: C#CCN1CCCc2ccc(OC(=O)N(C(C)C)C(C)C)cc21]

A solution of 1-(prop-2-ynyl)-1,2,3,4-tetrahydroquinolin-7-ol (400 mg, 2.14 mM) in dry tetrahydrofuran (THF; 5 mL) was added to the stirred solution of sodium hydride in dry THF at −10° C. during 5 minutes under nitrogen environment at room temperature (25° C.). The reaction mixture was stirred for 30 minutes. Then, N,N-diisopropyl carbamoyl chloride (510 mg) was added to the stirring reaction mixture. The mixture was stirred further for 7 hours during which the temperature was allowed to reach the room temperature (35° C.). The reaction mixture was diluted with ethyl acetate, washed with water, and dried over sodium sulphate. The combined fractions of ethyl acetate were concentrated under vacuum and chromatographed using ethyl acetate:hexane (1:49) to afford 10h as semisolid. Yield: 72.6%.

M.W. 314; Chemical Formula: $C_{19}H_{26}N_2O_2$; $^1$H-NMR (CDCl$_3$, 300 MHz). □6.91-6.88 (d, 2H), 6.33 (s, 1H), 4.43 (s, 2H), 3.31-3.28 (t, J=5.674 Hz, 2H), 3.05 (s, 14H), 2.77-2.72 (t, J=6.201 Hz, 2H), 2.13 (s, 1H), 2.03-1.93 (m, 2H). ESMS: m/z: 315 (M+1)$^+$ Pharmacological Activities Passive avoidance test is widely used as experimental model to assess learning and memory functions in rodents. Scopolamine induced impairment in passive avoidance (in vivo) and inhibition of acetylcholinesterase (in vitro) in rodents are commonly employed screening tests to predict potential of a compound as acetylcholinesterase inhibitor and anti-amnesic drug (Das et al., 2002).

Passive Avoidance Test (in vivo):

The study was conducted in adult Swiss albino male mice (20-25 g). Mice were kept in standard housing condition with 12 h light and dark cycle. The food and water were available ad libitum.

The passive avoidance test was carried out as described by Tota et al., 2009. The mice were subjected to the passive avoidance test by placing in a compartment with light at intensity of 8 [Scale from 0 to 10 (brightest)] in a computerized shuttle box with a software programme PACS 30 (Columbus Instruments, Ohio, USA).

The light compartment was isolated from the dark compartment by an automated guillotine door. After an acclimatization period of 30 s, the guillotine door was opened and closed automatically after entry of the mouse into the dark compartment. The subject received a low-intensity foot shock (0.5 mA; 10 s) in the dark compartment. Infrared sensors monitored the transfer of the animal from one compartment to another which was recorded as transfer latency time (TLT) in seconds. The $1^{st}$ trial was for acquisition and retention was tested in a $2^{nd}$ trial given 24 h after the $1^{st}$ trial. The duration of a trial was 270 s. The shock was not delivered in the retention trials to avoid reacquisition. A significant increase in the TLT on $2^{nd}$ trial (retention) as compared to $1^{st}$ trial (acquisition) was taken as the criterion for successful learning and memory.

Scopolamine Induced Memory Impairment (Amnesia):

Scopolamine, a muscarinic blocker known to produce impairment in cognitive functions in human as well as in experimental animals, was used to produce deficit (no significant increase on $2^{nd}$ trial) in passive avoidance learning. Scopolamine was administered 5 min prior to $1^{st}$ trial. Reversal of scopolamine induced deficit i.e. significant increase in TLT during $2^{nd}$ trial by test substance indicates potential anti-amnesic activity.

Drug Administration:

The standard drugs and test compounds were administered orally (1% aqueous suspension in gum acacia), 1 h prior to $1^{st}$ trial. Scopolamine control group received 10 ml/kg of vehicle (1% aqueous suspension in gum acacia) orally. Scopolamine (3 mg/kg, IP) was administered 5 min prior to 1st trial in test groups. Standard drugs tacrine (5 mg/kg, PO), donepezil (5 mg/kg, PO) and rivastigmine (2 mg/kg, PO) were given 1 h prior to 1st trial in mice. The test compound S009-073 was administered orally at 3.75, 7.5 and 15 mg/kg 1 hr prior to 1st trial.

Acetylcholinesterase (AChE) Assay in Brain (In Vitro)

The study was conducted in adult Swiss albino mice (20-25 g). The mice were perfused under mild ether anesthesia through heart with ice cooled normal saline (0.9% NaCl) to remove blood-born cholinesterase from the brain. After perfusion the whole brain was taken out. A 10% (w/v) homogenate of brain was prepared first by homogenizing in an Ultra-Turrax T25 homogenizer at a speed of 9500 rpm thrice giving intervals for few seconds in between the runs, with sodium phosphate buffer (0.03 M, pH-7)).

The brain homogenate in volume of 500 µl was mixed with 1% Triton X-100 (1% w/v in 0.03M sodium phosphate buffer, pH-7) and centrifuged at 100,000 g at 4° C. in a Beckman Ultracentrifuge (LE 80, USA), using a fixed angle rotor (80 ti) for 60 min. Supernatant was collected and stored at 4° C. for acetylcholinesterase estimation.

Enzyme Assay:

The assay of AChE was performed according to method described by Ellman et al., (1961). The kinetic profile of enzyme activity was measured spectrophotometrically (Shimadzu, USA) at 412 nm with an interval of 15 s. The assay for each sample was run in triplicate and each experiment was performed twice. The specific activity of AChE was calculated by following formula:

AChE activity=$\Delta E \times 1000 \times V/1.36 \times 10000 \times v$ $\Delta E$=Extinction change/min 1000=Conversion factor for µmoles $V$=Volume of the total reaction mixture 1.36×10000=Extinction Coefficient $v$=volume of the enzyme source used The specific activity of AChE is expressed in µM/min/mg of protein.

The test substance (dissolved in ethanol) was incubated with enzyme source in different concentrations (0.1-100 µmol) for 30 min at 37° C. prior to obtain kinetic profile of AChE activity. Tacrine and rivastigmine (0.1-100 µmol) were used as standard AChE inhibitor (standard control). The AChE inhibitory activity was calculated on the basis of % decrease in AChE activity from control values i.e. AChE activity without incubation with any standard or test drug.

Protein Assay:

Protein was estimated in the brain samples by modified Lowry's method (Wang and Smith, 1975). Bovine serum albumin (BSA) was used as standard.

Statistical Analysis:

The results are expressed as mean±S.E.M. Statistical analysis of passive avoidance values were performed by t-test. The $IC_{50}$ value was calculated by non linear regression method using GraphPad Prism software.

In Vitro AChE Inhibitory Activity

Figure 2:
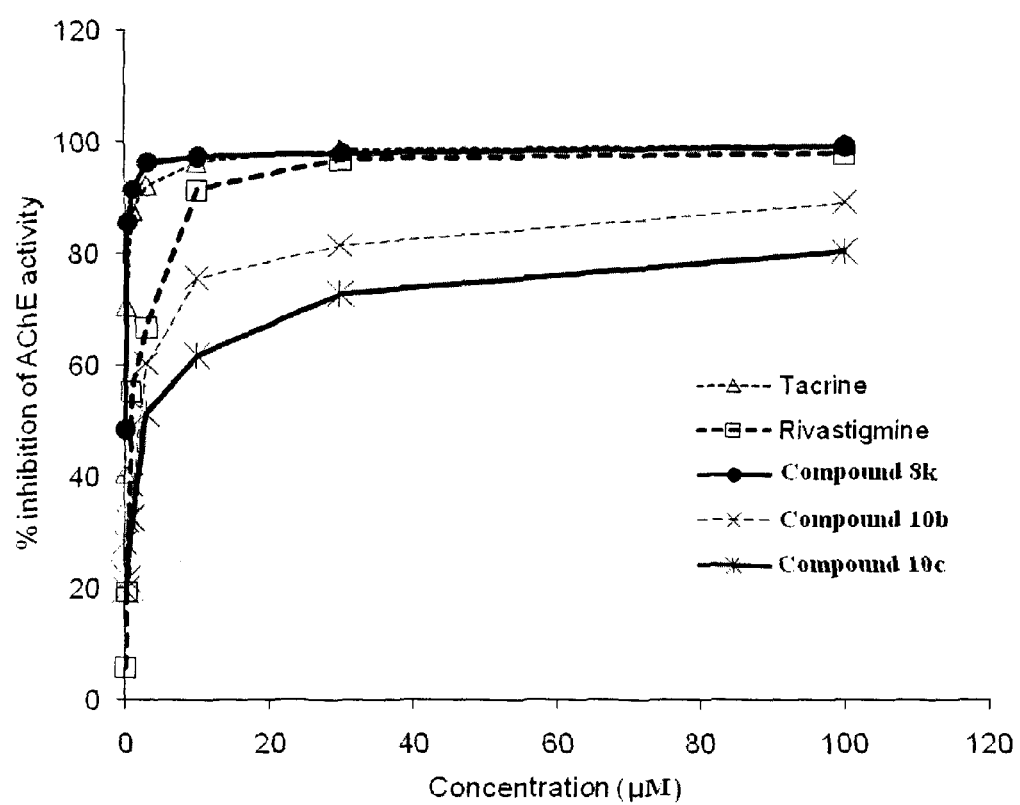
FIG. 2: A plot of % inhibition of AChE activity with the concentration of tested compounds and clinical drugs.

The in vitro AChE inhibitory activity of the title compounds along with the two reference compounds (Rivastigmine and Tacrine) determined using the spectrometric methods known as Ellman method are summarized in Table 1. The plot of percent AChE inhibition with the concentrations of the test compounds and the controls are shown in FIG. 2.

TABLE 1 in vitro Acetylcholinesterase (AChE) inhibitory activity

| Compd | % Inhibition of AChE enzyme | | AChE $IC_{50}$ ± SEM (µM) |
|---|---|---|---|
| | 10 µM | 100 µM | |
| 8a | 44.1 | 90.4 | 13.01 ± 0.66 |
| 8b | 5.412 | 25.1 | 354.1 ± 21.54 |
| 8c | 9.874 | 19.54 | >100 |
| 8d | 5.231 | 15.487 | >100 |
| 8f | 2.1 | 12.512 | >100 |
| 8h | 5.201 | 10.104 | >100 |
| 8i | 2.5 | 24.121 | 298.5 ± 12.69 |
| 8j | 1.41 | 3.591 | >100 |
| 8k | 95.48 | 98.03 | 0.099 ± 0.003 |
| 8l | 32.82 | 58.75 | 55.93 ± 2.97 |
| 9a | 0.01 | 1.447 | >100 |
| 9b | 10.516 | 55.712 | 76.3 ± 0.9 |
| 9c | 1.145 | 21.55 | 326.93 ± 15.93 |
| 9d | 1.86 | 38.92 | 126.13 ± 4.17 |
| 10a | 52.46 | 60.75 | 13.26 ± 3.33 |
| 10b | 55.47 | 77.15 | 7.59 ± 0.62 |
| 10c | 71.7 | 87.3 | 2.82 ± 0.04 |
| 10d | 17.87 | 22.51 | >100 |
| 10e | 95.37 | 96.26 | 0.92 ± 0.12 |
| 10f | 25.37 | 30.86 | 756.43 ± 208.1 |
| 10g | 94.18 | 96.54 | 0.68 ± 0.02 |
| Rivastigmine | 91.44 | 97.86 | 1.1 ± 0.05 |
| Tacrine | 94.31 | 98.68 | 0.13 ± 0.002 |

The compound 8k possessing o-tolyl group on the carbamate end has exhibited 12-fold better AChE inhibitory activity compared to the currently used drug rivastigmine and almost equal or even slightly better AChE inhibitory activity compared to the drug Tacrine (Table 1). Furthermore, compounds 10e and 10g exhibited slightly better AChE inhibitory activity than rivastigmine. Another compound 10c has exhibited almost equal AChE inhibitory activity as compared to the drug Rivastigmine, while the compound 10b has exhibited 7-fold lower AChE inhibitory activity compared to the drug Rivastigmine.

In Vivo Passive Avoidance Learning Test

The study was conducted in adult Swiss albino male mice (20-25 g). Scopolamine, a muscarinic blocker known to produce impairment in cognitive functions in human as well as in experimental animals, was administered 5 min prior to 1st trial. The standard drugs and test compounds were administered orally (1% aqueous suspension in gum acacia) 1 h prior to 1st trial. Standard drugs tacrine (5 mg/kg, PO), donepezil (5 mg/kg, PO) and rivastigmine (2 mg/kg, PO) were given 1 h prior to 1st trial in mice. The test compounds were was administered orally at 3.75, 7.5 and 15 mg/kg 1 hr prior to 1st trial.

Figure 3:
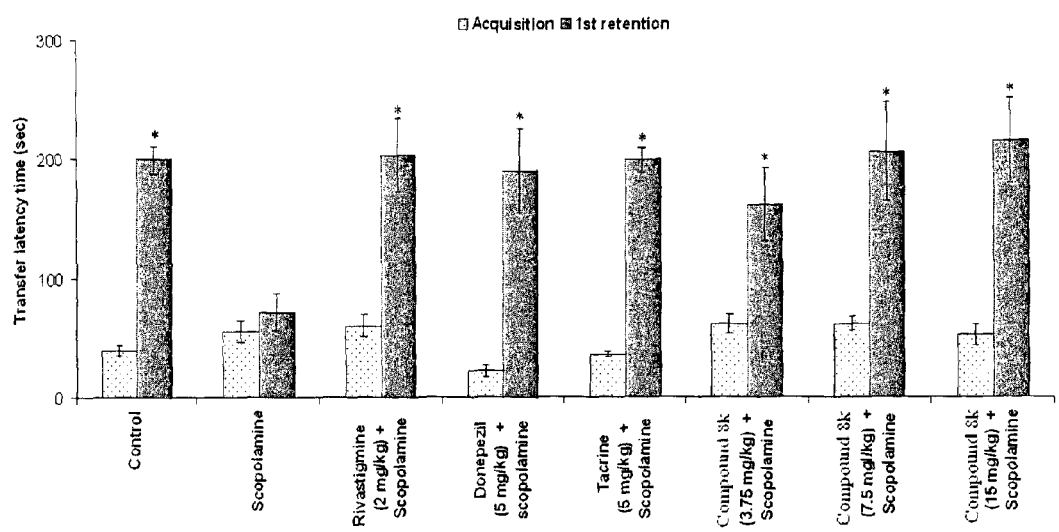
FIG. 3: Effect of CDRI compound (8k) on scopolamine induced amnesia in mice. Data values are expressed as mean TLT (sec)±S. E. M. *significant increase in transfer latency time (P<0.01) in comparison to acquisition trial.

The compound 8k, which has shown to have 10-fold better AChE inhibitory activity compared to the drug Rivastigmine, was tested in vivo using a behavioral study referred to as passive avoidance learning test conducted in Swiss albino male mice (weight: 20-25 g). As shown in FIG. 3, this compound (8k) has also shown potential towards the improvement in learning of mice and almost comparable to the drug Rivastigmine and Tacrine.

Gross Behavioral Study

Table 2 summarizes the gross behavioral study conducted in Swiss albino male mice (weight: 20-25 g). It was interesting to note that the compound 8k was found to be well tolerated upto the oral dose of 125 mg/kg and no cholinergic symptoms and mortality was observed upto 24 hrs of drug administration. The drugs Tacrine and donepezil were found to be well tolerated at 5 mg/kg dose, but with donepezil, moderate cholinergic symptoms were observed at 25 mg/kg dose and severe side effects were found initially at 50 mg/kg and all animals died within 24 hrs. The Rivastigmine was well tolerated at 1 mg/kg, and caused 100% mortality within 15 min at 4 mg/kg dose. At this latter dose, there was no detectable time gap between occurrence cholinergic side effect and death.

TABLE 2

Comparative analysis of the active compounds with the currently used drugs

| | |
|---|---|
| Rivastigmine | 1 mg/kg: No peripheral cholinergic symptoms. Overall locomotor activity was normal as control group. 2 mg/kg: 5-10 min after dosing animals become lethargic, dull and showed loss of grip and tachycardia but no salivation. This phase continues for 25-30 min and animals become normal one hr after dosing. 4 mg/kg: 100% mortality within 15 min of drug administration. There was no detectable time gap between occurrence cholinergic side effect and death. |
| Donepezil | well tolerated at 5 mg/kg dose. Moderate cholinergic symptoms were observed at 25 mg/kg. At 50 mg/kg severe side effects were found initially and all animals died within 24 hrs. |
| Tacrine | well tolerated at 5 mg/kg dose. |
| Compound 8k, 10b and 10e | Well tolerated at 125 mg/kg dose. No cholinergic symptom was observed upto 24 hrs of drug administration. |

Advantages

The compounds in the present invention are of better therapeutic efficacy and safety than the prior art drug rivastigmine. The compound 8k is free from any observable side peripheral side effect up to the oral dose of 125 mg/kg, while rivastigmine has exhibited some peripheral side effects at an oral dose of 3 mg/kg and showed 100% mortality of 42 male mice within 15 min of oral administration of 4 mg/kg. This compound is also better than other drugs such as donepezil and tacrine which belong to different classes.

We claim:

1. A compound of general formula A

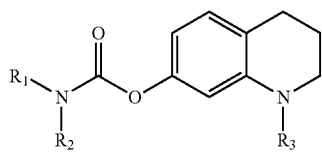

Formula A wherein:
$R_1$ and $R_2$, which may be identical or different, are selected from the group consisting of hydrogen, alkyl (C1-C2), mono- or di-substituted aryl;
$R_3$ is selected from the group, consisting of hydrogen, saturated or unsaturated alkyl (C1-C3), aryl, aralkyl, and alkynyl.

2. The compound as claimed in claim 1, wherein $R_1$ is alkyl, selected from the group consisting of methyl, isopropyl, hexyl and heptyl.

3. The compound as claimed in claim 1, wherein when $R_1$ is selected from the group consisting of 2-chlorophenyl, 3-chlorophenyl, 4-chlorophenyl, 2-bromophenyl, 3-bromophenyl, 4-bromophenyl, 2-fluorophenyl, 4-fluorophenyl, 2-isopropylphenyl, 2-methoxyphenyl, 4-methoxyphenyl, 2-methylphenyl, 3-methylphenyl, 4-methylphenyl, and 2-isopropyl-6-methylphenyl.

4. The compound as claimed in claim 1, wherein $R_1$ is alkyl and $R_2$ is selected from the group consisting of hydrogen, methyl, and isopropyl.

5. The compound as claimed in claim 1, wherein $R_2$ is substituted/unsubstituted aryl and $R_2$ is hydrogen.

6. The compound as claimed in claim 1, wherein, $R_3$ is selected from the group consisting of hydrogen methyl, prop-2-ynyl, and benzyl.

7. The compound as claimed in claim 1, wherein representative compounds of general formula A comprising:

1-benzyl-1,2,3,4-tetrahydroquinolin-7-yl 2-methylphenylcarbamate 8a;

1-benzyl-1,2,3,4-tetrahydroquinolin-7-yl 4-methylphenylcarbamate 8b;

1-benzyl-1,2,3,4-tetrahydroquinolin-7-yl 2-fluorophenylcarbamate 8c;

1-benzyl-1,2,3,4-tetrahydroquinolin-7-yl 4-fluorophenylcarbamate 8d;

1-benzyl-1,2,3,4-tetrahydroquinol 2-chlorophenylcarbamate 8e;

1-benzyl-1,2,3,4-tetrahydroquinolin-7-yl 4-chlorophenylcarbamate 8l;

1-benzyl-1,2,3,4-tetrahydroquinolin-7-yl hexylcarbamate 8g;

1-benzyl-1,2,3,4-tetrahydroquinolin-7-yl heptylcarbamate 8h;

1-benzyl-1,2,3,4-tetrahydroquinolin-7-yl 2-methoxyphenylcarbamate 8i;

1-benzyl-1,2,3,4-tetrahydroquinolin-7-yl 4-methoxyphenylcarbamate 8j;

1-benzyl-1,2,3,4-tetrahydroquinolin-7-yl dimethylcarbamate 8k;

1-methyl-1,2,3,4-tetrahydroquinolin-7-yl 2-fluorophenylcarbamate 8l;

1,2,3,4-tetrahydroquinolin-7-yl 4-methylphenylcarbamate 9a;

1,2,3,4-tetrahydroquinolin-7-yl 2-fluorophenylcarbamate 9b;

1,2,3,4-tetrahydroquinolin-7-y 4-fluorophenylcarbamate 9c;

1,2,3,4-tetrahydroquinolin-7-yl 4-chlorophenylcarbamate 9d;

1-(prop-2-ynyl)-1,2,3,4-tetrahydroquinolin-7-yl 2-methylphenylcarbamate 10a;

1-(prop-2-ynyl)-1,2,3,4-tetrahydroquinolin-7-yl heptylcarbamate 10b;

1-(prop-2-ynyl)-1,2,3,4-tetrahydroquinolin-7-yl 2-bromophenylcarbamate 10e;

1-(prop-2-ynyl)-1,2,3,4-tetrahydroquinolin-7-yl2-isopropyl-6-methylphenyl-carbamate 10d;

1-(prop-2-ynyl)-1,2,3,4-tetrahydroquinolin-7-yl 2-methoxyphenylcarbamate 10e;

1-(prop-2-ynyl)-1,2,3,4-tetrahydroquinolin-7-yl 4-chlorophenylcarbamate 10l;

1-(prop-2-ynyl)-1,2,3,4-tetrahydroquinolin-7-yl dimethylcarbamate 10g; or 1-(prop-2-ynyl)-1,2,3,4-tetrahydroquinolin-7-yl diisopropylcarbamate 10h.

8. The compound as claimed in claim 1, wherein the structures of representative compounds comprising:

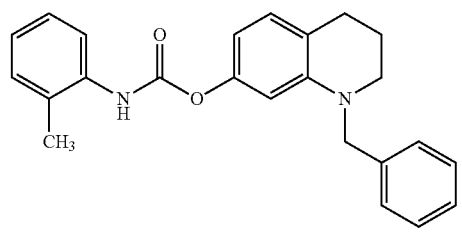 8a
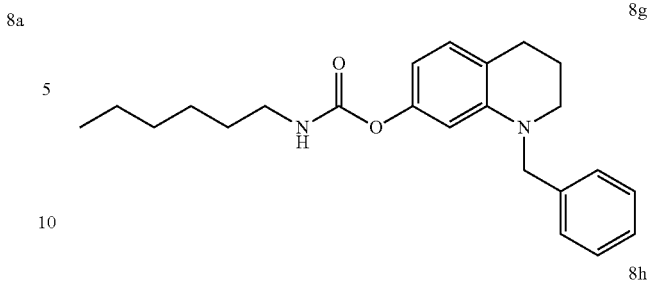 8g
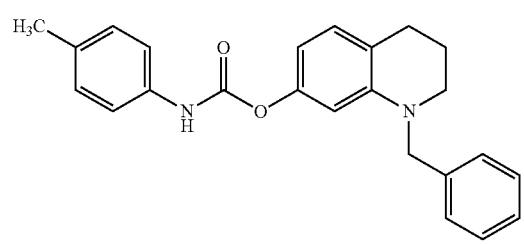 8b
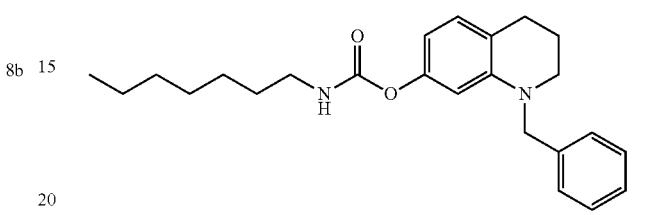 8h
8i
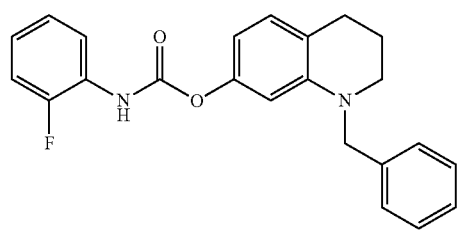 8c
 8j
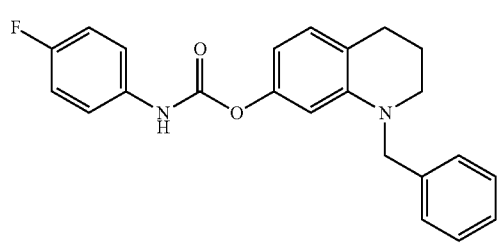 8d
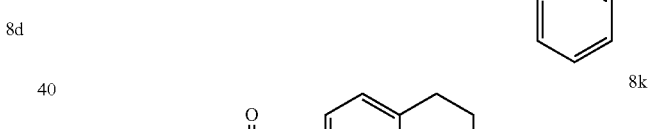 8k
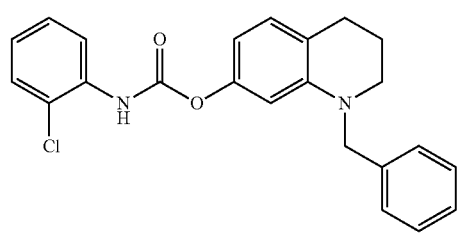 8e
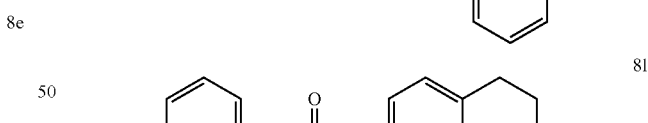 8l
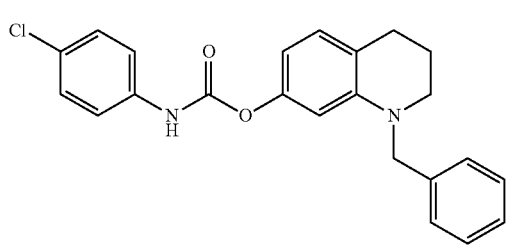 8f
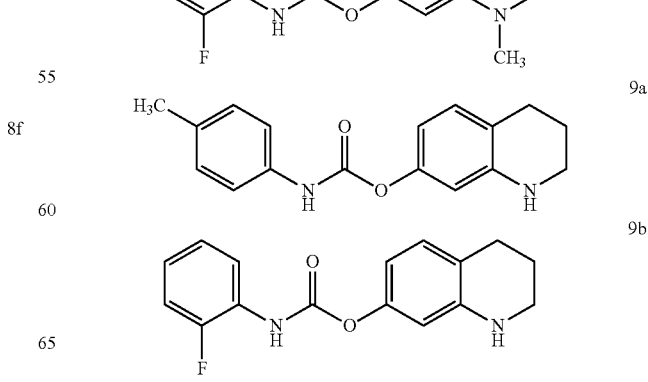
9a
9b

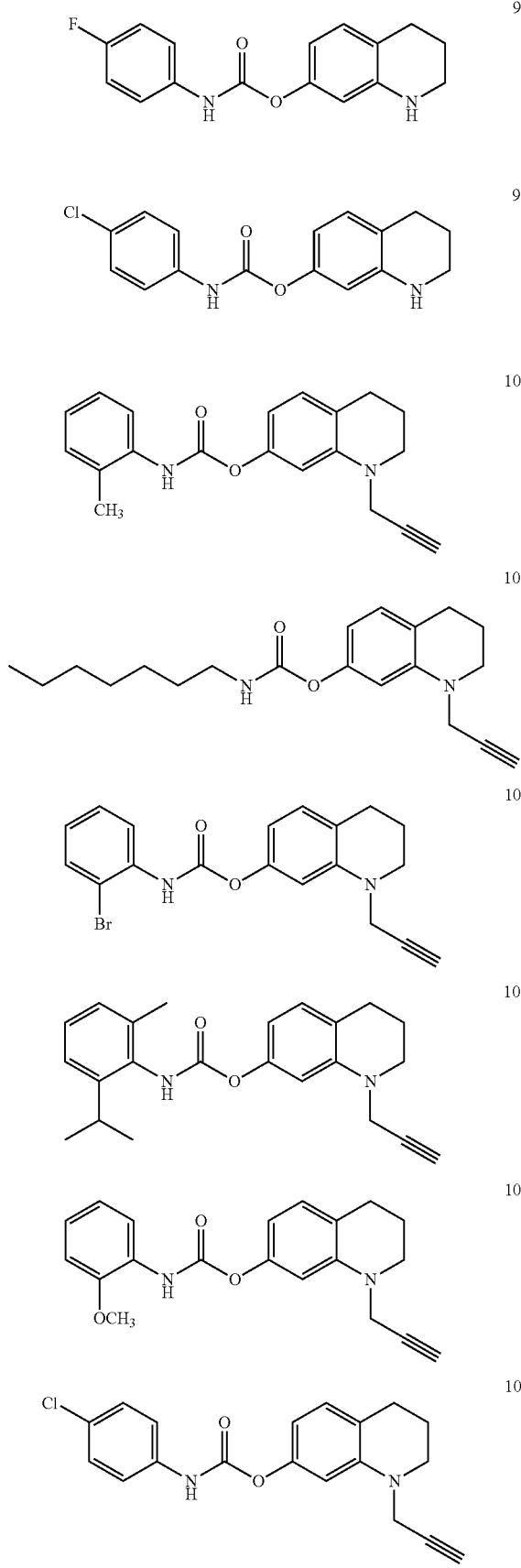
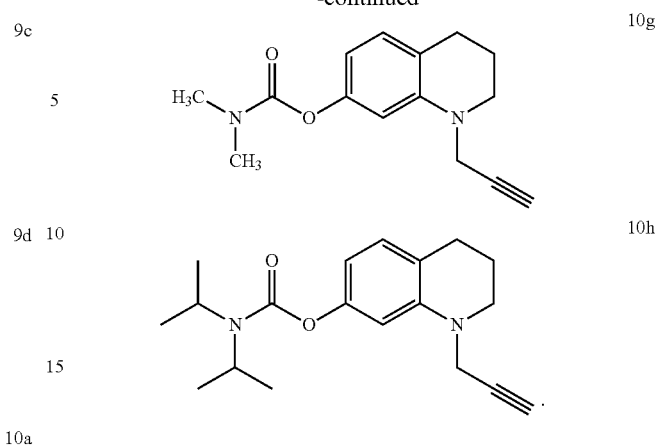

9. A process for the preparation of compound of Formula A as claimed in claim 1, wherein the process comprising
 a. mixing 1-substituted 1,2,3,4-tetrahydroquinolin-7-ol with a base and at least one organic solvent at a temperature in the range −10 to 60° C.;
 b. stirring the mixture as obtained in step (a) under inert atmosphere for a period in the range 5 ruins to 0.5 hrs;
 c. adding substituted aryl/alkyl isocyanate or N,N-substituted alkyl carbamoyl halide to the mixture as obtained from step (b);
 d. stirring the mixture as obtained in step (c) under inert atmosphere for a period in the range 3 to 48 hrs to obtain the substituted product;
 e. extracting and purifying the substituted product to obtain the compounds 8a-k or 10a-g;
 f. adding Pd—C 10% catalyst to the compounds 8b-e obtained from step (e) in the presence of a solvent by applying hydrogen pressure in the range of 50-60 psi for a period ranging between 4-12 hrs at a temperature ranging between 20 to 40° C. to obtain the compounds 9a-d.

10. The process as claimed in claim 9, wherein the base is selected from potassium carbonate, potassium iodide, triethylamine and sodium hydride.

11. The process as claimed in claim 9, wherein the organic solvent is selected from the group consisting of tetrahydrofuran (THF), dichloromethane (DCM) and dimethylformamide (DMF).

12. The process as claimed in claim 9, wherein nitrogen is used to create the inert atmosphere.

13. The process as claimed in claim 9, wherein substitution in substituted aryl/alkyl isocyanate is selected from the group consisting of hexyl, heptyl, 2-chlorophenyl, chlorophenyl, 4-chlorophenyl, 2-bromophenyl, 3-bromophenyl, 4-bromophenyl, 2-fluorophenyl, 4-fluorophenyl, 2-isopropylphenyl, 2-methoxyphenyl, 4-methoxyphenyl, 2-methylphenyl, 3-methylphenyl, 4-methylphenyl, 6-methylphenyl, and 2-isopropyl-6-methylphenyl.

14. The process as claimed in claim 9, wherein N,N-substituted alkyl carbamoyl halide is selected from the group consisting of N,N-dimethyl carbamoyl chloride and N,N-diisopropyl carbamoyl chloride.

15. The process as claimed in claim 9, wherein the solvent used in step (f) is selected from the group consisting of ethanol and methanol.

16. The process as claimed in claim 9, wherein compound of 81 can also be synthesized from 9b by reacting with methyl iodide in the presence of a base selected form a group consisting of potassium carbonate and potassium iodide in dimethylformamide as solvent and at a temperature ranging between −10 to 37° C.

17. The process as claimed in claim 9 wherein in 1-substituted-1,2,3,4-tetrahydroquinolin-7-ol, substituents at 1st position are selected from group consisting of methyl, propargyl and benzyl.

18. A pharmaceutical composition comprising therapeutically effective amount of a compound of general formula A as claimed in claim 1, optionally along with one or more pharmaceutically acceptable carriers, additives, lubricants and diluents.

19. A method for treating Alzheimer's disease (AD) in a subject comprising administering to a subject in need thereof a therapeutically effective amount of a compound of general formula A as claimed in claim 1.

20. A method for inhibiting acetylcholinesterase (AChE) enzyme in a subject comprising administering to a subject a compound of general formula A as claimed in claim 1.

21. The method for inhibiting acetylcholinesterase (AChE) enzyme according to claim 20, wherein the compound is administered in a concentration ranging between 0.09 to 7561 µM.

* * * * *